US012098193B2

(12) United States Patent
Cukierman et al.

(10) Patent No.: US 12,098,193 B2
(45) Date of Patent: Sep. 24, 2024

(54) NETRIN G1 AS A BIOMARKER FOR ENHANCING TUMOR TREATMENT EFFICACY

(71) Applicant: Institute For Cancer Research, Philadelphia, PA (US)

(72) Inventors: Edna Cukierman, Philadelphia, PA (US); Ralph Francescone, Philadelphia, PA (US); Janusz Franco-Barraza, Philadelphia, PA (US); Kristopher Raghavan, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 95 days.

(21) Appl. No.: 16/754,877

(22) PCT Filed: Oct. 9, 2018

(86) PCT No.: PCT/US2018/054994
§ 371 (c)(1),
(2) Date: Apr. 9, 2020

(87) PCT Pub. No.: WO2019/074915
PCT Pub. Date: Apr. 18, 2019

(65) Prior Publication Data
US 2021/0309729 A1     Oct. 7, 2021

Related U.S. Application Data

(60) Provisional application No. 62/570,694, filed on Oct. 11, 2017.

(51) Int. Cl.
*C07K 16/22* (2006.01)
*A61K 38/21* (2006.01)
*C07K 16/28* (2006.01)
*G01N 33/574* (2006.01)

(52) U.S. Cl.
CPC ............ *C07K 16/22* (2013.01); *A61K 38/217* (2013.01); *C07K 16/2818* (2013.01); *C07K 16/2827* (2013.01); *G01N 33/57484* (2013.01); *G01N 2800/7028* (2013.01); *G01N 2800/7052* (2013.01)

(58) Field of Classification Search
CPC ............... C07K 16/22; C07K 16/2818; C07K 16/2827; C07K 14/475; C07K 14/705; A61K 38/217; G01N 33/57484; G01N 2800/7028; G01N 2800/7052; G01N 33/574; C12Q 2600/158; C12Q 1/6883; C12Q 1/6886
See application file for complete search history.

(56) References Cited

U.S. PATENT DOCUMENTS

| 2010/0196426 A1* | 8/2010 | Skog ................... C12Q 1/6883 604/7 |
| 2011/0236903 A1* | 9/2011 | McClelland ......... C12Q 1/6886 435/6.1 |
| 2012/0178690 A1 | 7/2012 | Kennedy |
| 2014/0099340 A1 | 4/2014 | June et al. |

FOREIGN PATENT DOCUMENTS

| CA | 2988388 | 10/2016 |
| WO | 2011119484 | 9/2011 |
| WO | 2013040412 | 3/2013 |
| WO | 2016172722 | 10/2016 |
| WO | 2019074915 | 4/2019 |

OTHER PUBLICATIONS

Rollins. Netrin-G1 Enhances in Desmoplastic Fibroblasts Enhances Interactions with Pancreatic Cancer Cells. MS Dissertation Drexel University Jul. 2016, pp. 1-61, [online]. (Retrieved on Nov. 27, 2018] (Year: 2016).*
Rollins, D. "Netrin G1 in Desmoplastic Fibroblasts Enhances Interactions with Pancreatic Cancer Cells", 2016, Drexel University College of Medicine, 1-59. (Year: 2016).*
Sherman, MH et. al. "Vitamin D Receptor-Mediated Stromal Reprogramming Suppresses Pancreatitis and Enhances Pancreatic Cancer Therapy", 2014, Cell, 159(1), 1-27. (Year: 2014).*
Jia, J et. al. "FAP-α (Fibroblast activation protein-α) is involved in the control of human breast cancer cell line growth and motility via the FAK pathway", 2014, BMC Cell Biology, 15(16), 1-14. (Year: 2014).*
Cukierman et al., "Taking cell-matrix adhesions to the third dimension", Science, 2001, 294(5547), pp. 1708-1712.
Francescone et al., "The NetrinG1/NGL-1 Axis promotes pancreatic tumorigenesis through cancer associated fibroblast driven nutritional support and immunosuppression", BioRxiv, 2018, doi: http://dx.doi.org/10.1101/330209, pp. 1-60.
Franco-Barraza et al., "Matrix-regulated integrin avb5 maintains a5b1-dependent desmoplastic traits prognostic of neoplastic recurrence", eLife, 2017, 6, pp. e20600.

(Continued)

*Primary Examiner* — Nelson B Moseley, II
*Assistant Examiner* — Alyssa Rae Stonebraker
(74) *Attorney, Agent, or Firm* — Armstrong Teasdale LLP

(57) ABSTRACT

The present disclosure provides methods of inducing desmoplastic stroma to express a normal phenotype by detecting increased levels of NetG1 or NGL1 in tumor or in desmoplastic stroma isolated from a human subject, and/or detecting NetG1 in circulating extracellular vesicles, and/or detecting increased pFAK in the stroma, and treating the human subject with a therapeutic regimen; and by detecting NetG1 in a microvesicle isolated from a human subject, and/or treating the human subject with a therapeutic regimen.

4 Claims, 35 Drawing Sheets

(56) References Cited

OTHER PUBLICATIONS

Lu et al., "The MLL1-H3K4me3 Axis-Mediated PD-L1 Expression and Pancreatic Cancer Immune Evasion", J Natl Cancer Inst, 2017, 109(6), pp. 1-12.
Rollins, "Netrin G1 in Desmoplastic Fibroblast Enhances Interactions with Pancreatic Cancer Cells", MS Dissertation Drexel University, Jul. 2016, pp. 1-61.
Valente et al., "Distribution of interferon-gamma receptor in human tissues", Eur J Immunol, 1992, 22, pp. 2403-2412.
International Search Report and Written Opinion for PCT Application PCT/US2018/054994.
Seiradake et al., "Structural basis for cell surface patterning through NetrinG&ndashl NGL interactions", The EMBO Journal, 2011, 30(21), pp. 4479-4488.
Goldman et al., "The clasp between NetrinG and NGL becomes crystal clear", The EMBO Journal, 2011, 30(21), pp. 4342-4344.
Francescone et al., "Abstract 2038: NG1/NGL1 engagement supports PDAC development via CAF to PDAC nutrition and CAF-regulated immunosuppression", Cancer Research, 2019, 79, pp. 2038.
Niimi et al., "Monoclonal antibodies discriminating netrin-G1 and netrin-G2 neuronal pathways", K Neuroimmunol, 2007, 192(1-2), pp. 99-104.

\* cited by examiner

B.

C.

D.

A.

B.

C.

C.

A.

D.

E.

B.

A.

B.

C.

D.

E.

F.

G.

A.

KC model

B.

C.

D.

A.

C1-CAFs EVs probed with Anti-NetG1

C2-CAFs EVs probed with Anti-NetG1

C2-CAFs EVs probed for anti-NetG1 (Qdot; arrow,
small EVs) & anti-activated $\alpha_5\beta_1$-integrin (dense gold
particles; exosome size Evs)

B.

C.

NETRIN G1 AS A BIOMARKER FOR ENHANCING TUMOR TREATMENT EFFICACY

REFERENCE TO GOVERNMENT GRANTS

This invention was made with government support under Grant Nos. CA113451 and CA223539 awarded by the U.S. National Institutes of Health and Grant No. W81XWH-15-1-0170 awarded by the U.S. Army Medical Research and Materiel Command. The government has certain rights in the invention.

FIELD

The disclosure relates generally to the field of cancer and chronic fibrosis treatments. More particularly, the disclosure relates to detecting netrin G1 as a biomarker of active desmoplasia and of chronic fibrosis, which prompts treatment to revert the active desmoplasia to a normal phenotype, or which prompts an alteration of a standard of care that would otherwise have reduced efficacy due to the presence of the active desmoplasia.

BACKGROUND

Pancreatic ductal adenocarcinoma (PDAC) is fast becoming the second most lethal cancer in the United States. A specific PDAC characteristic is desmoplasia, which is a unique fibrous microenvironmental reaction that includes the expansion of activated stellate cells, known as cancer associated fibroblasts (CAFs), and the active remodeling of their extracellular matrix. PDAC's desmoplasia is typically hypo-angiogenic and immunosuppressive to both cytotoxic T and natural killer (NK) cells. Cell-cell interactions between PDAC, CAFs and immune cells, within the desmoplastic milieu, are not fully understood.

Desmoplastic stroma plays a role in epithelial tumor development and progression such as, for example, in pancreatic or renal epithelial tissue. The exact contribution of the mesenchymal stroma for the development of a pro-tumorigenic role for desmoplasia is not clear. Nonetheless, homeostatic normal or innate mesenchymal stroma is believed to provide a natural tumor suppressive microenvironment. Evidence has emerged that desmoplastic ablation is detrimental to patients. Other evidence indicates that reprograming mesenchymal stroma back to its restrictive innate state seems to bear therapeutic promise, including reinstituting anti-tumoral immune activity. Thus, desmoplasia has potential implications for tumor therapy. There remains a need in the art to be able to manipulate desmoplastic stroma, toward improving the understanding of the underlying biology behind stromal activation.

It was previously shown that extracellular matrices (ECMs) produced by fibroblastic naive and activated cells (e.g., tumor- or cancer-associated fibroblasts; known as TAFs or CAFs, respectively) present phenotypes that are reminiscent of in vivo quiescent tumor restrictive and activated/desmoplastic stroma. Similarly, it was previously demonstrated that desmoplastic ECM (D-ECM) can serve as pathophysiological relevant substrates capable of activating naive/innate fibroblasts. There further remains a need to harness the role that desmoplasia plays in cancer development and progression, toward improving patient outcomes.

SUMMARY

In the present disclosure, the ectopic expressions of NetrinG1 (NetG1 or NetG1), a neural pre-synaptic protein, in CAFs, and of NetG1's post-synaptic binding partner, NetrinG1 ligand (NGL1), in PDAC cells is described. Using a multi-cellular 3D culturing system, heterotypic CAF-to-PDAC cell-cell interactions, via NetG1/NGL1 engagement, were discovered to be critical for providing survival advantages to nutrient-deprived PDAC cells and for CAFs to protect PDAC from NK cell-driven elimination. It was further discovered that PDAC starvation was overcome by NetG1-expressing CAF produced ECMs and by NetG1-expressing CAFs that provide nutrition via material transfer, based on an intact glutamine/glutamate cycle. Further, CRISPR/CAS9 mediated knockout of NetG1, in CAFs, significantly reduced the production of both immunosuppressive cytokines, like IL-6 and IL-8, pro-tumor immunosuppressive factors like TGFβ, and other pro-tumorigenic factors, such as GM-CSF and CCL20. Moreover, loss of NetG1 from CAFs resulted in, anti-tumor, NK cells activation. These results were confirmed in an orthotopic PDAC mouse model in which ablation of NGL1, in syngeneic mouse PDAC cells, significantly halted tumor growth and metastasis. The presence of the NetG1, NGL1, or the combination of both in patient samples (tumor surgical or bodily fluids) may provide information regarding drug efficacies as well as early detection or predisposition of tumors and evidence for this is also disclosed. There are no effective therapies for pancreatic cancer, demonstrated by the abysmal 5-year survival rate of around 7-8%. The present disclosure provides methods to limit the stroma's ability to metabolically support tumor cells, as well as harness the immune system to attack cancer cells.

The present disclosure provides methods of inducing desmoplastic stroma to express a normal phenotype comprising: detecting increased levels of NetG1 in desmoplastic stroma isolated from a human subject; and/or detecting NetG1 in circulating extracellular vesicles; and/or detecting increased focal adhesion kinase activity (pFAK) in the stroma; and treating the human subject with a therapeutic regimen.

The present disclosure also provides methods of inducing desmoplastic stroma to express a normal phenotype comprising: detecting NetG1 in a microvesicle isolated from a human subject; and/or treating the human subject with a therapeutic regimen.

The present disclosure also provides methods of treating a human subject having chronic fibrosis or cancer comprising: detecting increased levels of NetG1 (or NGL1) in desmoplastic stroma isolated from the human subject; and/or detecting NetG1 in circulating extracellular vesicles; and/or detecting increased pFAK in the human subject; administering to the human subject an amount of interferon gamma effective to prime T lymphocytes and/or NK cells; isolating desmoplastic stroma or liquid biopsy from the pancreas, kidney or others after a period of time following the administering of the interferon gamma or other agent; detecting decreased levels of NetG1 and/or NGL1 in the isolated desmoplastic stroma or liquid biopsy; detecting decreased pFAK in the stroma; and administering to the human subject an effective amount of an antibody that specifically binds to PD-1 or to PD-L1 or other immune checkpoint inhibitors or one that specifically binds to NetG1 or to NGL1, thereby treating the chronic fibrosis or cancer.

The present disclosure also provides methods of treating a human subject having chronic fibrosis or cancer comprising: detecting increased levels of NetG1 (and/or NGL1) in microvesicles isolated from the human subject; administering to the human subject an amount of interferon gamma effective to prime T lymphocytes and/or NK cells; isolating microvesicles from the human subject after a period of time following the administering of the interferon gamma or other agent; detecting decreased levels of NetG1 (and/or NGL1) in the isolated microvesicles; and administering to the human subject an effective amount of an antibody that specifically binds to PD-1 or to PD-L1 or other immune checkpoint inhibitors or one that specifically binds to NetG1 or to NGL1, thereby treating the chronic fibrosis or cancer.

The present disclosure also provides methods of detecting the presence or absence of NetG1 and/or NGL1 in a sample from a human subject, wherein the presence of NetG1 and/or NGL1 in an amount greater than a healthy control indicates that the subject has chronic fibrosis or cancer.

The present disclosure also provides methods of monitoring therapeutic efficacy of cancer treatment comprising detecting the presence or absence of NetG1 and/or NGL1 in a sample from a human subject, wherein an increase in NetG1 and/or NGL1 compared to previously measured levels of NetG1 and/or NGL1 indicates that the current treatment regimen is underperforming whereas a decrease in NetG1 and/or NGL1 compared to previously measured levels of NetG1 and/or NGL1 indicates that the current treatment regimen is performing satisfactorily.

DESCRIPTION OF EMBODIMENTS

Figure 1:
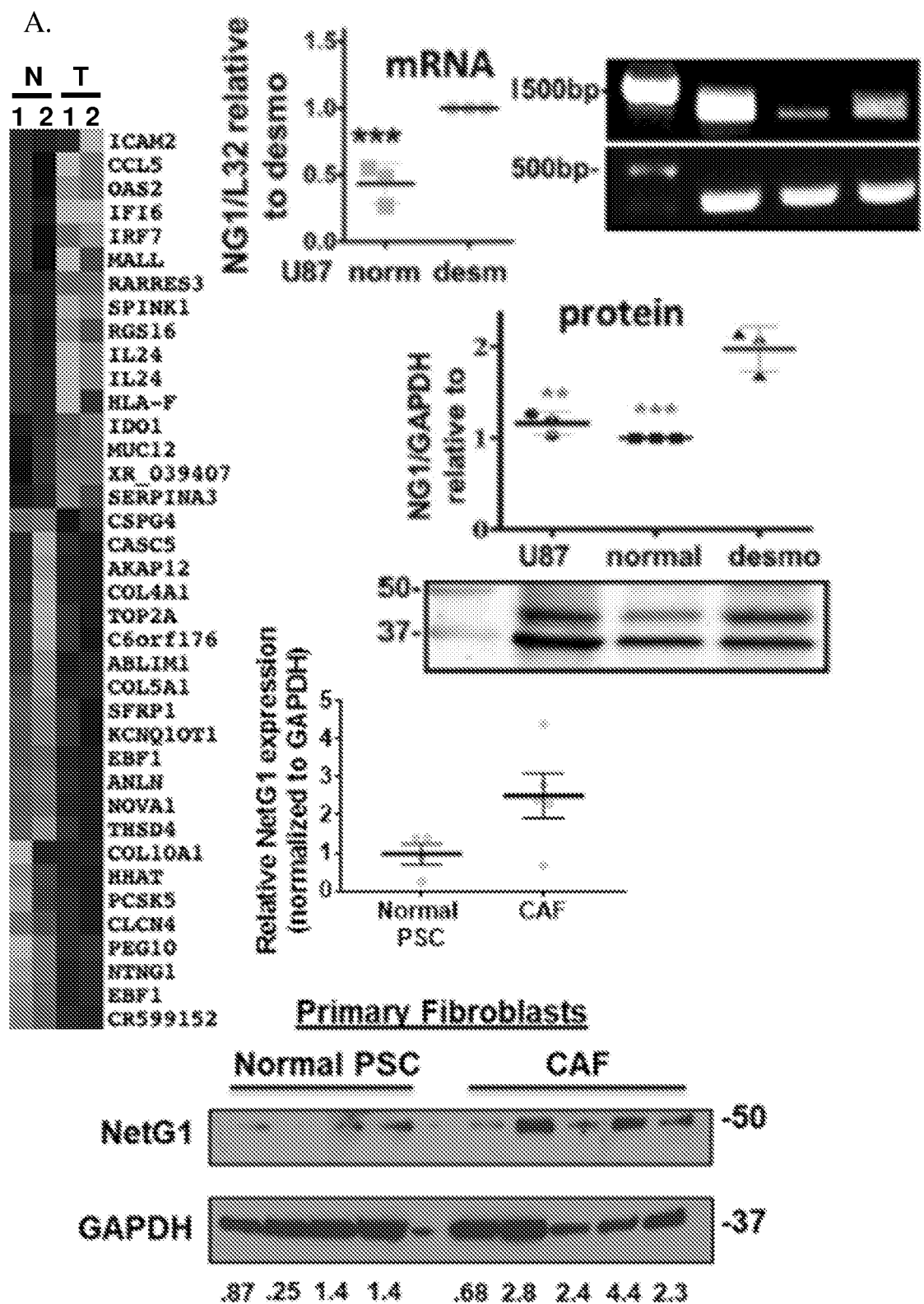
FIG. 1 (panels A, B, C, and D) show NetG1 is upregulated in CAFs, and its binding partner NGL1 is upregulated in pancreatic cancer cells (PDAC). Also, analysis of tissue samples from PDAC patients show a correlation between NetG1 in the stroma and NGL-1 in the tumor, and a correlation between stromal pFAK in the stroma and NetG1 in the stroma.
Figure 1:
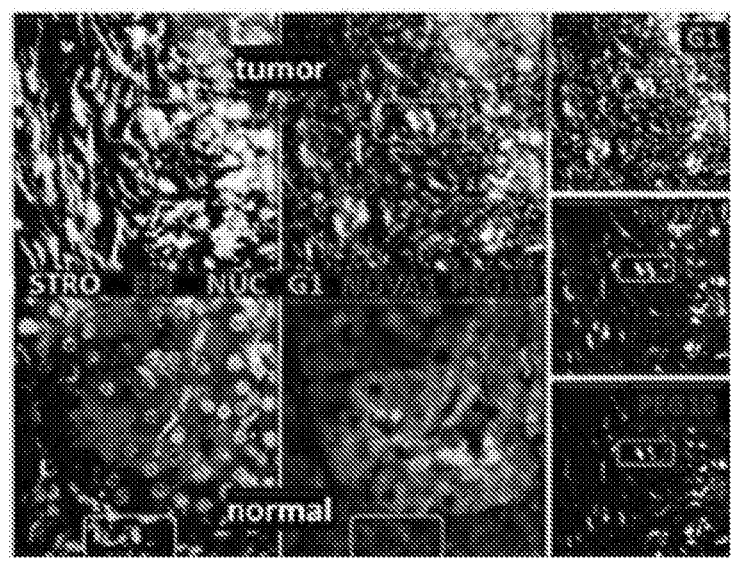
Figure 1:
Figure 1:
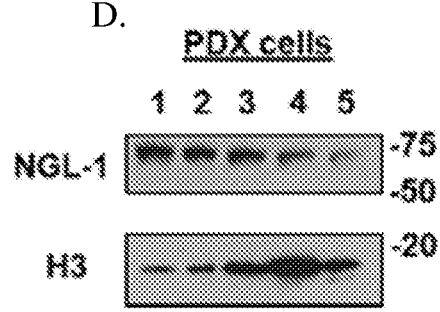
Figure 1:
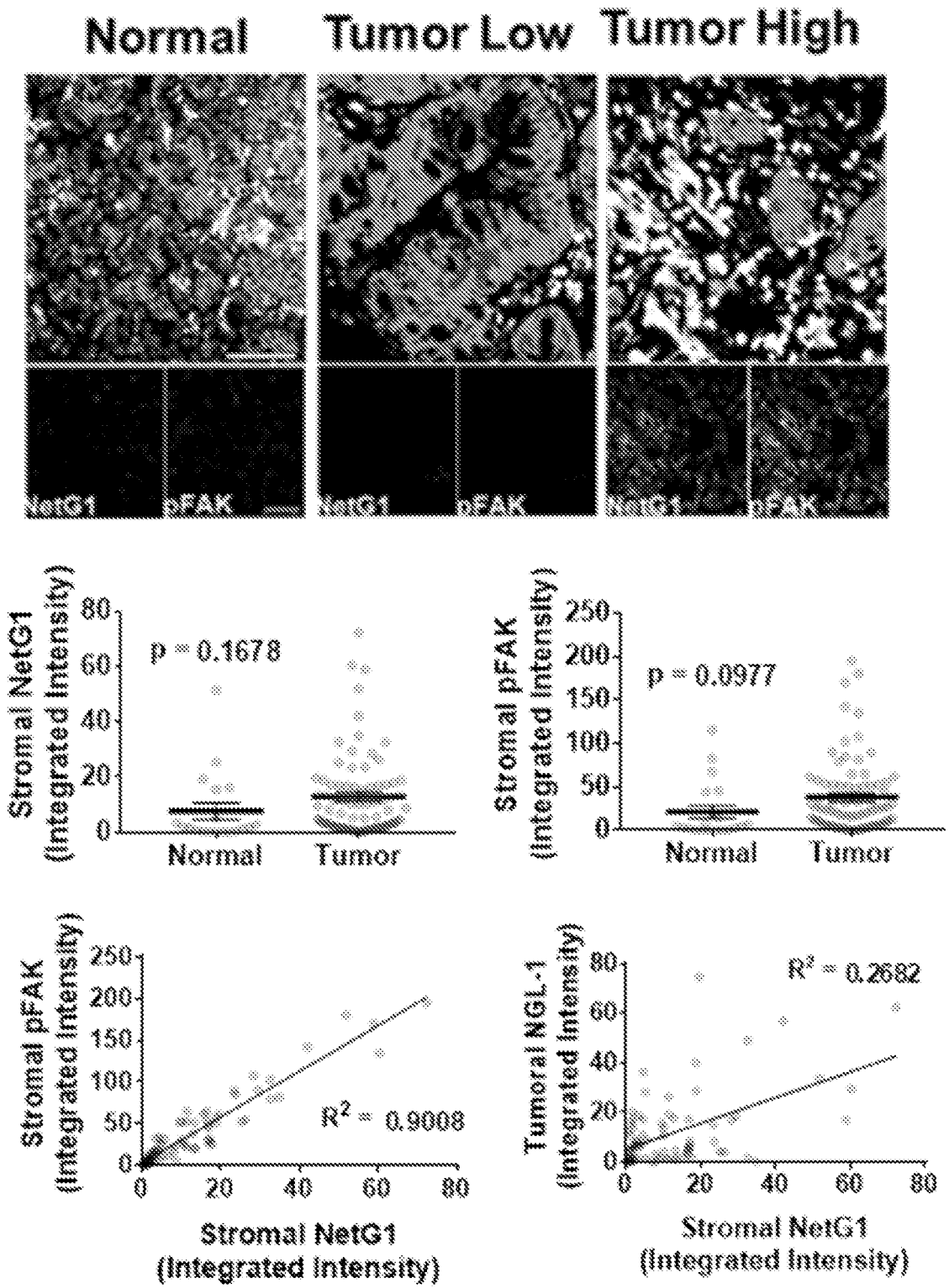

Various terms relating to embodiments of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

A material has been "isolated" if it has been removed from its natural environment and/or altered by the hand of a human being.

The terms "subject" and "patient" are used interchangeably. A subject may be any animal, such as a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). In some embodiments, the mammal is a human.

Using pancreatic ductal adenocarcinoma (PDAC) and renal cell carcinoma (RCC) as well as a murine skin stromal models, the experiments described herein assessed the potential dynamic manipulation of both D-ECMs and their ability to induce fibroblastic activation. It was observed that the levels and localization of NetG1 together with levels of FAK activity (phosphor FAK; pFAK) may serve as a biomarker indicative of active desmoplasia, which is patient-detrimental. Similarly active alpha5beta1-integrin localized at 3D-adhesion structures represents the "protective" phenotype which is predictive of disease recurrence in pancreatic cancer patients following surgery. Further, levels of NetG1 in desmoplasia correlate with pFAK and integrin traits and, thus, are also prognostic prompts. This biomarker combinatorial approach, with special emphasis on levels of NetG1 and/or NGL1, may be used to detect the development of early stage cancers associated with fibrosis predisposition, fibrosis per se, or to assess patient risk, as well as to predict the efficacy of chemotherapy or to alter a treatment course to enhance efficacy that would have been impaired given the presence of active desmoplasia, as well as to predict tumor recurrence. Identification of active desmoplasia or fibrosis may be further useful, for example, in distinguishing between benign stroma (NetG1 (and/or NGL1) low and detrimental desmoplasia; high NetG1 (and/or NGL1) expressing desmoplasia. It was further observed that the detection of active desmoplasia (via the level and localization of NetG1) coupled with increased focal adhesion kinase (FAK) activity (pFAK) can be used to stage desmoplasia. Accordingly, the present disclosure provides methods for reverting active, detrimental desmoplasia to a normal/innate phenotype, as well as methods for treating tumors associated with fibrosis or fibrosis per se. Any of the methods may be carried out in vivo, in vitro, or in situ.

NetG1 is only expressed ectopically in pancreatic stroma if such cells are cultured within their own derived extracellular matrices (ECMs). In addition, NetG1 and NGL1 are neural proteins that have only been studied in the brain. Thus, their role in tumor biology, such as in the pancreas, is unexpected because nearly all current research on NetG1 (and/or NGL1) is focused on its mechanism of action in neurons and the brain.

The present disclosure provides methods of inducing desmoplastic stroma to express a normal phenotype comprising: detecting increased levels of NetG1 in desmoplastic stroma isolated from a human subject; and/or detecting NetG1 in circulating extracellular vesicles; and/or detecting increased pFAK in the stroma; and treating the human subject with a therapeutic regimen.

In some embodiments, the therapeutic regimen: inhibits fibroblast activation; inhibits the biologic activity of transforming growth factor (TGF) beta; inhibits the pathological expression of NetG1 in pancreatic stroma; blocks chronic fibrosis or inflammation; is a neutralizing antibody (or binding peptide) against the activity of αVβ5-integrin or NetG1; an agent that prevents increase of palladin isoform 4 overexpression or expression of palladin isoform 3; an agent that prevents NetG1 to engage with tumoral NGL1; an agent that lowers expression of NetG1 or NGL1; an agent that prevents signaling from NetG1; an agent that inhibits leukocyte antigen receptor (LAR) phosphatase; or an agent that prevents the plasma membrane localization of NetG1 or NGL1; thereby inducing the desmoplastic stroma to express a normal phenotype. Such treatments induce the desmoplastic stroma to express a normal/innate phenotype. Such treatments may also include administration of vitamin D or vitamin D analogs to the subject, in an amount effective to induce the desmoplastic stroma to express a normal/innate phenotype, or impede the biological activity of TGF beta, or impeding the biologic activity of fibroblastic NetG1, or other anti-fibrotic treatments, using biochemical or small molecules inhibitors in an amount effective to induce the desmoplastic stroma to switch to and/or express a normal/innate phenotype.

In some embodiments, the NetG1 is NetG1m, NetG1a, NetG1c, NetG1n, NetG1o, NetG1b, NetG1d, NetG1e, NetG1l or any other alternative form of NetG1.

In some embodiments, the step of detecting increased levels of NetG1 comprises contacting the isolated desmoplastic stroma with an antibody that specifically binds to NetG1 or with soluble NGL1 that specifically binds to NetG1. In some embodiments, the desmoplastic stroma is contacted with an antibody that specifically binds to NetG1.

In some embodiments, the methods further comprise isolating desmoplastic stroma from the lung, prostate, breast, liver, pancreas, kidney or other organ(s) of the subject by taking a biopsy.

In some embodiments, the biopsy is a liquid biopsy, core needle biopsy, or a surgical biopsy.

In some embodiments, the desmoplastic stroma from the lung, prostate, breast, liver, pancreas, kidney or other organ (s) is cancerous. In some embodiments, the desmoplastic stroma from the organ is cancerous.

The present disclosure also provides methods of inducing desmoplastic stroma to express a normal phenotype comprising: detecting NetG1 in a microvesicle isolated from a human subject; and/or treating the human subject with a therapeutic regimen.

In some embodiments, the therapeutic regimen: inhibits fibroblast activation; inhibits the biologic activity of TGF beta; inhibits the pathological expression of NetG1 in pancreatic stroma; blocks chronic fibrosis or inflammation; is a neutralizing antibody against the activity of αVβ5-integrin or NetG1; an agent that prevents increase of palladin isoform 4 overexpression or expression of palladin isoform 3; an agent that prevents fibroblastic NetG1 engagement to NGL1; an agent that lowers expression of NetG1 or NGL1; an agent that prevents or alters signaling from NetG1; an agent that inhibits leukocyte antigen receptor (LAR) phosphatase; or an agent that prevents the plasma membrane localization of NetG1; thereby inducing the desmoplastic stroma to express a normal phenotype.

In some embodiments, the NetG1 is present within blood, plasma, ascites, urine, or saliva.

In some embodiments, the step of detecting NetG1 (and/or NGL1) comprises contacting NetG1 (and/or NGL1) with an antibody that specifically binds to NetG1 (and/or to NGL1) or with soluble NGL1 that specifically binds to NetG1. In some embodiments, NetG1 is contacted with an antibody that specifically binds to NetG1.

In some embodiments, the microvesicle is from the lung, prostate, breast, liver, pancreas, kidney or other organs. In some embodiments, the lung, prostate, breast, liver, pancreas, kidney or other organ is cancerous.

The present disclosure also provides methods of treating a human subject having chronic fibrosis or cancer comprising: detecting increased levels of NetG1 (and/or NGL1) in desmoplastic stroma isolated from the human subject; and/or detecting NetG1 in circulating extracellular vesicles; and/or detecting increased pFAK in the human subject; administering to the human subject an amount of interferon gamma effective to prime T lymphocytes and/or Natural killer cells; isolating desmoplastic stroma or liquid biopsy from the pancreas, kidney or other organ after a period of time following the administering of the interferon gamma or other agent; detecting decreased levels of NetG1 (and/or NGL1) in the isolated desmoplastic stroma or liquid biopsy; detecting decreased pFAK in the stroma; and administering to the human subject an effective amount of an antibody that specifically binds to PD-1 or to PD-L1 or other immune checkpoint inhibitors or that specifically binds to NetG1 or to NGL1 or prevents their engagement, thereby treating the chronic fibrosis or cancer.

In some embodiments, the cancer is lung cancer, prostate cancer, breast cancer, liver cancer, pancreatic cancer, kidney cancer or any other desmoplasia bearing cancer.

In some embodiments, the methods further comprise treating the human subject with a therapeutic regimen.

In some embodiments, the therapeutic regimen: inhibits fibroblast activation; inhibits the biologic activity of TGF beta; inhibits the pathological expression of NetG1 (or NGL1); blocks chronic fibrosis or inflammation; is a neutralizing antibody against the activity of αVβ5-integrin or NetG1 or NGL1; an agent that prevents induction of increased palladin isoform 4 overexpression or expression of palladin isoform 3; an agent that prevents NetG1 from engaging with NGL1; an agent that lowers expression of NetG1 or NGL1; an agent that prevents signaling from desmoplastic NetG1; an agent that inhibits leukocyte antigen receptor (LAR) phosphatase; or an agent that prevents the plasma membrane localization of NetG1 and/or NGL1; thereby inducing the desmoplastic stroma to express a normal phenotype.

In some embodiments, the step of detecting increased levels of NetG1 comprises contacting the isolated desmoplastic stroma with an antibody that specifically binds to NetG1 or using soluble NGL1 or similar that specifically binds to NetG1. In some embodiments, the desmoplastic stroma is contacted with an antibody that specifically binds to NetG1 and/or NGL1 In some embodiments, the methods further comprise isolating desmoplastic stroma from the lung, prostate, breast, liver, pancreas, kidney or other organs of the subject by taking a biopsy.

In some embodiments, the biopsy is a liquid biopsy, core needle biopsy, or a surgical biopsy.

In some embodiments, the desmoplastic stroma from the lung, prostate, breast, liver, pancreas, kidney or other organ (s) is cancerous. In some embodiments, the desmoplastic stroma from the organ is cancerous.

The present disclosure also provides methods of treating a human subject having chronic fibrosis or cancer comprising: detecting increased levels of NetG1 in microvesicles isolated from the human subject; administering to the human subject an amount of interferon gamma effective to prime T lymphocytes and/or Natural killer cells; isolating microvesicles from the human subject after a period of time following the administering of the interferon gamma or other agent; detecting decreased levels of NetG1 in the isolated microvesicles; and administering to the human subject an effective amount of an antibody that specifically binds to PD-1 or to PD-L1 or other immune checkpoint inhibitors or that specifically binds to NetG1 or to NGL1, thereby treating the chronic fibrosis or cancer.

In some embodiments, the cancer is lung cancer, prostate cancer, breast cancer, liver cancer, pancreatic cancer, kidney cancer or other desmoplastic bearing cancer.

In some embodiments, the methods further comprise treating the human subject with a therapeutic regimen.

In some embodiments, the therapeutic regimen: inhibits fibroblast activation; inhibits the biologic activity of TGF beta; inhibits the pathological expression or function of NetG1; blocks chronic fibrosis or inflammation; is a neutralizing antibody against the activity of αVβ5-integrin or NetG1; an agent that prevents increase of palladin isoform 4 overexpression or expression of palladin isoform 3; an agent that prevents fibroblasticNetG1 from engaging with NGL1; an agent that lowers expression of NetG1 or NGL1; an agent that prevents or alters signaling from NetG1; an agent that inhibits leukocyte antigen receptor (LAR) phosphatase; or an agent that prevents the plasma membrane localization of NetG1 or NGL1; thereby inducing the desmoplastic stroma to express a normal phenotype as measured by pFAK and/or alpha5beta1 activated integrin.

In some embodiments, the step of detecting increased levels of NetG1 comprises contacting the microvesicles with an antibody that specifically binds to NetG1 or using soluble NGL1 or similar that specifically binds to NetG1. In some embodiments, the microvesicles are contacted with an antibody that specifically binds to NetG1.

In some embodiments, the methods further comprise isolating microvesicles from the lung, prostate, breast, liver, pancreas, kidney or other organs of the subject by taking a biopsy.

In some embodiments, the biopsy is a liquid biopsy, core needle biopsy, or a surgical biopsy.

In some embodiments, the lung, prostate, breast, liver, pancreas, kidney or other organ is cancerous. In some embodiments, the pancreas or kidney is cancerous.

In any of the methods described herein, the stroma may be isolated from any suitable tissue in the subject. The tissue may comprise pancreatic tissue (e.g., pancreatic stroma), kidney tissue (e.g., kidney stroma), or lung tissue (e.g., lung stroma). The tissue may comprise any tissue, including epithelial tissue, from any organ, having stroma. The tissue may be fibrotic, cancerous, or may be pre-cancerous, or may be suspected of being cancerous or pre-cancerous. The assessment of the stroma need not be related to cancer, for example, the stroma may be isolated for determining a fibrosis condition, including pulmonary or lung fibrosis, renal/kidney fibrosis, or pancreatic fibrosis. Stroma may be isolated from the tissue according to any suitable isolation technique. A biopsy may be used in some embodiments. For example, a surgical biopsy may be used, or a core needle biopsy may be used. In addition to or in the alternative to solid tissue sampling, the assessments of NetG1 and/or NGL1) may be carried out in liquid samples, including liquid biopsies. Thus, in some embodiments, liquid biopsies are obtained from the subject.

In any of the methods described herein, for embodiments involving a liquid biopsy, the blood or ascites fluid, or any other suitable biologic fluid such as saliva, gingival crevicular fluid, urine, sweat, tears, spinal fluid, etc. of a subject may be isolated and screened. From such isolated biologic fluids, stromal microvesicles may be isolated. The biopsy methods may comprise detecting NetG1 (and or NGL1) in a microvesicle from the blood or ascites fluid (or other suitable biologic fluid), thereby determining whether stroma in the subject includes active or tumor-protective desmoplasia. In some embodiments, if NetG1 is detected, particularly concomitantly with the detection of high pFAK levels (as a proxy for active desmoplasia), then the subject is treated with a therapeutic regimen as described herein. In some embodiments, the methods further comprise solubilizing the microvesicle. In any of the methods described herein, the detection of NetG1 may comprise contacting the isolated stroma with antibodies that specifically bind to NetG1. Such antibodies are: N2C1 antibody from GeneTex Cat #GTX115637), D-2 from Santa Cruz (Cat #sc-271774) or any antigen-binding fragment thereof. Before screening with the antibody, the isolated stroma may be digested with appropriate enzymes to aid in retrieving the antigen and maintain the NetG1 in its conformation.

In any of the methods described herein, from the liquid biopsies, the detection of NetG1 (and or its partner NGL1)

may comprise contacting the microsome, or contents thereof, with antibodies that specifically bind to a conformation of NetG1. Such antibodies are N2C1, D-2 or any antigen-binding fragment thereof. Before screening with the antibody, the liquid biopsy may be treated with appropriate detergents (e.g., Triton®, SDS, NP 40, or other suitable detergent).

The liquid biopsies assess microvesicles shed from the stroma. In some embodiments, when liquid biopsies are screened, the methods may or may not include pFAK and/or NGL1 assessments. The microvesicles and/or any other type of extracellular vesicles may be shed from the stroma of a cancerous or pre-cancerous tissue. The tissue may be any tissue from which stroma may shed microvesicles, and may include pancreatic tissue, kidney tissue, or lung tissue or other organs' tissue. Thus, the treatments may be directed to desmoplastic stroma as pancreatic desmoplastic stroma, kidney desmoplastic stroma, or lung desmoplastic stroma, or any other desmoplastic stroma.

Immune priming may be a part of a treatment regimen, and may affect desmoplasia and the stroma, thereby having implications for adjustments to the treatment regimen, or may indicate that the stroma has reverted from an immunosuppressive state to a state of anti-tumor immune competency. Without intending to be limited to any particular theory or mechanism of action, it is believed that immune priming may induce stroma changes, including a reduction in the level of active desmoplasia or an alteration on the stroma microstructure sufficient to diminish the immune privileged (or immunosuppressive) nature of activated stroma. It is believed that immune priming-induced stroma changes are reflected in decreasing levels of NetG1 and/or decreasing levels of pFAK in the stroma.

Immune priming includes the pre-activation of immune cells that participate in cell-mediated immunity, including T cells, NK cells and other peripheral blood mononuclear cells (PBMC) such as monocytes and granulocytes. Cell-mediated immunity constitutes an important defense against cancer, though many cancers exhibit countermeasures that thwart the immune system's efforts. Immune priming treatments generally include administration of an activator of the immune cells of interest to a subject in need thereof. Immune cytokines may be used as the priming activator, including interferons (or inhibiting the immunossupressive aspect of desmoplasia by hampering NetG1 or NGL1 dependent desmoplastic immunossupression) In certain cancers, the PD-1/PD-L1/L2 pathway or similar immune checkpoints play a role in the tumors avoiding attack by the immune system. For example, PD-1 inhibitors, a relatively new category of cancer therapeutics, enhance the immune system attack by inhibiting the tumor's capacity to escape immune destruction. PD-1 inhibiting antibodies such as nivolumab and pembrolizumab bind to PD-1 and inhibit the PD-1/PD-L1 pathway. Gamma interferon increases PD-L1 levels.

The immune privileged nature of active stroma (e.g., stroma with high levels of NetG1 and pFAK) is believed to inhibit tumor-killing immune cells from accessing the tumor. In such cases, even PD-1/PD-L1/L2-ready cells (e.g., cells treated with inhibitors such as nivolumab and pembrolizumab) would still be impeded from tumor destruction by the stroma, particularly an active stroma. Accordingly, it is believed that immune priming, such as the priming achieved by gamma interferon treatment, can induce stromal changes sufficient to weaken the stroma impediment to immune system-mediated tumor destruction. In this way, PD-1/PD-L1/L2-ready cells can gain access to the tumor. But if not, then treatments such as NetG1 inhibition or other anti-fibrotic treatments (TGF-beta-like or other anti-inflammatory treatments) may assist.

As time is of the essence in any cancer treatment regimen, it is helpful to know when the tumors are most vulnerable or, on alternately, when the tumor's innate defenses such as an activated stroma will impede the regimen. Thus, detection of active stroma (e.g., active desmoplasia) will further the goal of identifying treatment impediments and/or of knowing when the tumor's defenses are down. In this respect, the active desmoplasia-detecting modalities of this disclosure are useful to furthering these goals. For example, the detecting modalities may be used to determine when the stroma is most likely to impede an immunotherapy treatment regimen (e.g., because the stroma is in a stage of active desmoplasia and is immune privileged), and may further be used to determine when the stroma or active desmoplasia has been diminished sufficiently to garner immunotherapy success.

The present disclosure also provides methods of detecting the presence or absence of NetG1 and/or NGL1 in a sample from a human subject, wherein the presence of NetG1 and/or NGL1 in an amount greater than a healthy human control indicates that the subject has chronic fibrosis or cancer. Blood (or other fluid) from a human subject may be used to measure the amount of the protein of interest, which would be circulating in microsomes or exosomes or other types of extracellular vesicles released from cancer associated fibroblasts (CAFs). An inverse correlation between the expression level of the protein of interest and patient survival and a direct correlation with disease severity is expected. If elevated levels of NetG1 (as a proxy for active desmoplasia) is detected, then the subject is treated with a therapeutic regimen as described herein. The subject may be treated with, for example, an amount of interferon, such as gamma interferon, effective to both prime immune cells such as T lymphocytes and/or NK cells and to revert the desmoplastic stroma to express a normal phenotype. In some embodiments, after a period of time sufficient to at least prime the immune cells, stroma is again isolated from the subject, followed by detecting decreased levels of NetG1, and detecting decreased pFAK in the stroma, thereby determining whether the isolated stroma includes diminished active desmoplasia (e.g., relative to the increased levels of active desmoplasia before interferon or similar treatment). If the levels of active desmoplasia are decreasing in the subject or benign, protective levels are increasing, the method may comprise administering to the subject an effective amount of an antibody that specifically binds to PD-1 or to PD-L1, including nivolumab and/or pembrolizumab (or similar). Administering such an antibody thereby treats the cancer in the subject. The cancer may be any cancer capable of being treated with antibodies to PD-1 or PD-L1 or similar. The cancer may be kidney cancer, pancreatic cancer, or lung cancer or any other desmoplastic bearing cancer.

The present disclosure also provides methods of monitoring therapeutic efficacy of cancer treatment comprising detecting the presence or absence of NetG1 and/or NGL1 in a sample from a human subject, wherein an increase in NetG1 and/or NGL1 compared to previously measured levels of NetG1 and/or NGL1 indicates that the current treatment regimen is underperforming whereas a decrease in NetG1 and/or NGL1 compared to previously measured levels of NetG1 and/or NGL1 indicates that the current treatment regimen is performing satisfactorily. It is believed that high endogenous (e.g., intracellular) levels of NetG1 represent active detrimental desmoplasia or fibrosis. Thus, the detection of active desmoplasia may also be used to guide treatments of other conditions, including cancer or a fibrosis condition. The levels of NetG1 may be monitored before, during, and after treatment, for example, to assist in guiding a therapeutic regimen (e.g., chemotherapy) or to assess the efficacy of treatments for reverting the active desmoplasia to a normal/innate phenotype. In such cases, the chemotherapy regimen may be adjusted to take into account high levels of active desmoplasia, or to take into account diminishing levels of active desmoplasia, for example, where treatments successfully revert the desmoplasia to a normal/innate phenotype. Adjustments include, for example, one or more of adjustments to dosing, administration scheduling, starting time, drug types, and other relevant considerations attendant to therapy.

The present disclosure also provides methods comprising isolating desmoplastic stroma from one or more of the pancreas, kidney, lung, or other epithelial tissue that may bear desmoplastic reaction, of a human subject, detecting increased levels of NetG1, detecting increased pFAK or NGL1 in the stroma, treating the subject with a therapeutic regimen that inhibits one or more of fibroblast activation, the biologic activity of TGF beta, or the biologic activity of NetG1 in one or more of the pancreatic stroma, kidney stroma, lung stroma, or stroma of other tissue, or regimen that blocks chronic fibrosis or inflammation, thereby inducing the desmoplastic stroma to express a normal/innate phenotype. In some embodiments, the treatment comprises administering to the subject vitamin D or a vitamin D analog, or impeding the biological activity of TGF beta, or impeding the biologic activity of desmoplastic NetG1, or other anti-fibrotic treatments, using biochemical or small molecules inhibitors in an amount effective to induce the desmoplastic stroma to switch to and/or express a normal/innate phenotype. In some embodiments, increased levels of NetG1 is detected by contacting the isolated desmoplastic stroma with an antibody that specifically binds to Net1. In some embodiments, the antibodies that specifically bind to NetG1 are N2C1, D-2, a binding fragment thereof or a NetG1 peptide or molecule.

In some embodiments, isolating desmoplastic stroma comprises taking a biopsy of one or more of the pancreas, kidney, lung or other organ. The biopsy may comprise a core needle biopsy or a surgical biopsy. The pancreas, kidney, lung or other organ being assessed in the subject may be cancerous.

The present disclosure also provides methods comprising isolating microvesicles from the blood and/or ascites fluid (or any other suitable biologic fluid such as saliva, gingival crevicular fluid, urine, sweat, tears, spinal fluid, etc.) of a human subject, detecting NetG1 (levels, localization and/or co-expression with pFAK and other proteins indicative of desmoplasia and/or chronic fibrosis) in the microvesicle, and then treating the subject with a therapeutic regimen that inhibits one or more of fibroblast activation, the biologic activity of TGF beta, or the biologic activity of NetG1 or NGL1 in desmoplastic stroma, or regimen that blocks chronic fibrosis or inflammation, thereby inducing the desmoplastic stroma to express a normal phenotype. In some embodiments, the treatment comprises administering to the subject vitamin D or a vitamin D analog in an amount effective to induce the desmoplastic stroma to express a normal/innate phenotype. The treatment may comprise administering to the subject vitamin D or a vitamin D analog, or impeding the biological activity of TGF beta, or impeding the biologic activity of desmoplastic NetG1, or other anti-fibrotic treatments, using biochemical or small molecules inhibitors in an amount effective to induce the desmoplastic stroma to switch to a normal/innate phenotype.

In some embodiments, the method comprise solubilizing the microvesicle or detecting NetG1 at the membrane of the extracellular vesicle (e.g., microvesicle) with an antibody that specifically binds to NetG1. In some embodiments, the antibodies that specifically bind to netrin G1 are N2C1 and/or D-2 antibodies.

Such liquid biopsies, which generally are less invasive than solid tissue biopsies, may be used to detect the presence of active desmoplasia in one or more of the pancreas, kidney, lung or any other organ of the subject. The pancreas, kidney, lung or any other organ being assessed in this way may be cancerous.

The present disclosure also provides methods comprising isolating desmoplastic stroma from one or more of a cancerous pancreas, cancerous kidney, or cancerous lung, or other cancerous epithelial tissue of a human subject, detecting increased levels of NetG1, and detecting increased pFAK or NGL1 in the stroma, and administering to the subject an amount of interferon gamma (or similar) effective to prime T lymphocytes and/or NK cells. In some embodiments, the methods comprise re-isolating desmoplastic stroma from one or more of the cancerous pancreas, cancerous kidney, or cancerous lung or other cancerous epithelial tissue from the subject after a period of time following the administering of interferon gamma or similar, detecting decreased levels of NetG1, and detecting decreased pFAK or NGL1 in the stroma, and administering to the subject an effective amount of an antibody that specifically binds to PD-1 or to PD-L1 (or similar), thereby treating the cancerous pancreas, cancerous kidney, or cancerous lung, or other cancerous epithelial tissue. In some embodiments, the methods further comprise treating the subject with a therapeutic regimen that inhibits one or more of fibroblast activation, the biologic activity of TGF beta, or the biologic activity of NetG1 in pancreatic stroma, kidney stroma, or lung stroma, or regimen that blocks chronic fibrosis or inflammation, thereby inducing the desmoplastic stroma to express a normal/innate phenotype. In some embodiments, such treatment comprises administering to the subject vitamin D or a vitamin D analog, or impeding the biological activity of TGF beta, or impeding the biologic activity of desmoplastic NetG1, or other anti-fibrotic treatments, using biochemical or small molecules inhibitors in an amount effective to induce the desmoplastic stroma to switch to a normal/innate phenotype. In some embodiments, detection of increased or decreased levels of NetG1 comprises contacting the isolated desmoplastic stroma with one of the antibodies that specifically bind to netrin G1, such as N2C1 and D-2 antibodies.

Isolating and re-isolating desmoplastic stroma may comprise taking a biopsy of one or more of the cancerous pancreas, kidney, or lung or other cancerous epithelial tissue. The biopsy may comprise a core needle biopsy or a surgical biopsy.

The present disclosure also provides methods comprising isolating microvesicles from the blood and/or ascites fluid (or any other suitable biologic fluid such as saliva, gingival crevicular fluid, urine, sweat, tears, spinal fluid, etc.) of a human subject, detecting increased general levels of NetG1 in the stromal or fibrous microvesicle, and administering to the subject an amount of interferon gamma effective to prime T lymphocytes and/or NK cells, or other agent suitable for priming T lymphocytes and/or NK cells. In some embodiments, the methods comprise isolating a second microvesicle from the blood or ascites fluid (or any other suitable biologic fluid such as saliva, gingival crevicular fluid, urine, sweat, tears, spinal fluid, etc.) of a human subject after a period of time following the administering of interferon gamma (or any other agent suitable for priming T lymphocytes or other immune cells), detecting decreased vesicular levels of NetG1 in the microvesicle, and administering to the subject an effective amount of an antibody that specifically binds to PD-1 or to PD-L1 (or similar immune checkpoint inhibitors), thereby treating the cancerous pancreas, cancerous kidney, cancerous lung or any other cancerous organ. In some embodiments, the methods further comprise treating the subject with a therapeutic regimen that inhibits one or more of fibroblast activation, the biologic activity of TGF beta, or the biologic activity of NetG1 in pancreatic stroma, kidney stroma, lung stroma, or any other organ stroma or regimen that blocks chronic fibrosis or inflammation, thereby inducing the desmoplastic stroma to express a normal phenotype. In some embodiments, such treatment comprises administering to the subject vitamin D or a vitamin D analog, or impeding the biological activity of TGF beta, or impeding the biologic activity of NetG1, or other anti-fibrotic treatments, using biochemical or small molecules inhibitors in an amount effective to induce the desmoplastic stroma to switch to a normal/innate phenotype. In some embodiments, detection of increased or decreased levels of netrin G1 comprises contacting the isolated desmoplastic stroma with an antibody that specifically binds NetG1, such as N2C1 or D-2 antibody. In some embodiments, the methods comprise immuno-isolating (e.g., to select for N2C1-positive and/or D-2 positive vesicles) and/or solubilizing the microvesicle.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Materials and Methods

Cell lines. Fibroblastic cells were cultured at 37° C. under 5% $CO_2$ using Dulbecco's Modified Eagle's Medium (Mediatech (Manasas, VA)) supplemented with 10-15% (murine-human, respectively) Premium-Select Fetal Bovine Serum (Atlanta Biologicals (Lawrenceville, GA)), 2 mM L-Glutamine, and 100 u/ml-μg/ml Penicillin-Streptomycin. Pancl, $FAK^{+/+}$, $FAK^{-/-}$, SYF and littermate wild type control cells were obtained from the American Tissue Culture Collection (Manassas, VA). FAK-KD and hTert controls were a gift.

Isolation and Characterization of fibroblastic cells. Pankeratin-negative (AE1/AE3-Dako (Carpinteria, CA)) and vimentin-positive fibroblastic cells (EPR3776-Abcam (Cambridge, MA)) were isolated from fresh surgical normal and tumor tissue samples, and sorted as normal or activated. Cells were used for no longer than 12 passages while maintained within their own derived ECMs.

Preparation of fibroblasts-derived 3D ECMs. Extracellular matrices (ECMs) were obtained in the presence or absence of TGFβ1R small molecule inhibitor SB431542, DMSO, and NetG1 antibody, or species matched non-immunized isotypic antibodies. Un-extracted 3D cultures were either processed for phenotypic characterization, ECM alignment measurements, or decellularized to assess maintenance of myofibroblastic phenotype.

ECM prompted myofibroblastic maintenance. Human naive or assorted murine fibroblasts were incubated for 45 minutes prior to overnight culturing within assorted ECMs, prepared as above, in the presence or absence of 50 μg/ml NetG1 antibody 250 μg/m mAb16, or BMA5 diluted as instructed by the manufacturer (Millipore, Temecula, CA), IgG control, DMSO or small molecule inhibitors FAK (PF573,228) and SRC family kinases (PP2). ECM-induced phenotypes were assessed via RT-qPCR, Western Blot or immunofluorescence.

Confocal Image Acquisition. Confocal spinning disk Ultraview (Perkin-Elmer Life Sciences, Boston, MA) images were acquired with a 60× (1.45 PlanApo) oil immersion objective, under identical exposure conditions per channel using Velocity 6.3.0 (Perkin-Elmer Life Sciences, Boston, MA). Maximum reconstruction projections were obtained using MetaMorph 7.8.1.0 (Molecular Devices, Downingtown, PA).

ECMfiber orientation analysis. Fibronectin channel monochromatic images were analyzed via ImageJ' OrientationJ plugin. Numerical outputs were normalized by setting mode angles to 0° and correcting angle spreads to fluctuate between −90° and 90°. Angle spreads for each experimental condition, corresponding to a minimum of three experimental repetitions and five image acquisitions per condition were plotted and their standard deviations calculated. The percentage of fibers oriented between −15° and 150 was determined for each normalized image-obtained data.

Bioinformatics and Statistics. Non-parametric Mann-Whitney tests were used to question experimental significances of all in vitro data. Significant p values in all figures were denoted by asterisks as follow: ** P<0.0001 extremely significant, * P=0.0001-0.01 very significant, ** P=0.01-0.05 significant and * P=0.06-0.10 marginally significant.

Regarding statistics pertinent to the TMAs, in order to identify clinical variables related to patient survival, univariate and multivariable analyses were performed by constructing decision trees using the Classification and Regression Trees (CART) methodology. Clinical variables were considered as predictors of survival time. The unified CART framework that embeds recursive binary partitioning into the theory of permutation tests was used. Significance testing procedures were applied to determine whether no significant association between any of the clinical variables and the response could be stated or whether the recursion would need to stop. No correction for multiple testing was employed, and a Type I error of 5% was used to test each hypothesis.

SMIA Processes.

Conjugation of Q-dot to primary antibody. Q-dot antibody labeling kits were obtained from Molecular Probes-ThermoFisher Scientific. The SiteClick labeling kit constitutes a three step procedure lasting a few days and requires to have the desired antibody's carbohydrate domain modified to allow an azide molecule to be attached to it and in consequence DIBO-modified nanocrystals are linked to the antibody in question. Each conjugation was carried out as instructed by manufacturer provided protocols. Briefly, approximately 100 μg of antibody was used in each case. Unless there were excessive carrier proteins present in the antibody there was no need for antibody pre-purification step. The labeled antibodies were estimated at 1 μmolar concentration and stored in sterile conditions at 4° C. in light protected boxes. Sample incubations were all performed at a final concentration of ~20 nMolar or 1:50 dilution.

Immunolabeling of FFPE tissue sections. Slides were exposed to short wave UV lamp for about 30 minutes in light protected box to quench auto fluorescence. They were then kept in a light protected (i.e., dark) box until used. Sections were deparaffinized in xylene and rehydrated in ascending graded alcohol to water dilutions. Sections were then treated with Digest-All (Invitrogen) and permeabilized in 0.5% TRITON® X-100 non-ionic surfactant. After treating them with blocking buffer as in vitro samples were first incubated with the above-mentioned Q-dot pre-labeled antibodies overnight at 4° C. Sections were washed as in vitro and incubated with a mix of mouse monoclonal "cocktail" containing anti-pan-cytokeratin (clones AE1/AE3, DAKO), anti-EpCam (MOC-31EpCam, Novus Biologicals (Littleton, CO)) and anti-CD-70 (113-16 Biolegend (San Diego, CA)), to detect epithelial/tumoral locations, together with rabbit monoclonal anti-vimentin (EPR3776, Abcam) antibodies (mesenchymal stromal components) for 2 hours at room temperature.

Pre-incubated Q-dot labeled antibodies could no longer be recognized by secondary antibodies thus allowing for indirect immunofluorescent detection of tumoral and stromal masks. Secondary antibodies were as in vitro and included donkey anti-mouse Cy2 and donkey anti-rabbit Cy3. Nuclei were stain using Draq-5 (as in vitro). Sections were quickly dehydrated in graded alcohol and clarified in Toludene before mounting in Cytoseal-60. Slides were cured overnight at room temperature before the imaging.

Image acquisitions of FFPE fluorescently labeled sections. FFPE sections of biological samples are known to give strong broad autofluorescence thus obscuring the specific (labeled) fluorescent signal. To overcome this problem, images were collected using Caliper's multispectral imaging system (PerkinElmer) which utilizes a unique imaging module with tunable Liquid Crystal. Two different systems namely Nuance-FX (for 40× objective) and Vectra (for 20× objective and high throughput) were used depending on the acquisition needs. A wavelength length based spectral library for each system and each tissue type (i.e., pancreas and kidney) was created by staining control sections with individual fluorophores or mock treating samples to including the specific autofluorescence spectra. Once a spectral library was constructed per organ type it was saved and used for the subsequent image acquisition and analysis. All excitations were achieved via high intensity mercury lamp using the following filters (emission-excitation): for Nuance, DAPI (450-720), FITC (500-720), TRITC (580-720), CY5 (680-720); for Vectra, DAPI (440-680), FITC (500-680), TRITC (570-690), CY5 (680-720). For emissions collection: "DAPI" filter (wavelength range 450-720) was used for all Q-dot labeled markers, while masks used the conventional FITC, TRITC and CY5 filters. After collecting all image cubes (including all channels) images were unmixed to obtain 16 bit greyscale individual stains monochromatic files. Using Photoshop's Levels and Batch Conversion Functions the images were processed in bulk to render identically scaled 8 bit monochromatic images per channel. The resulting images were sampled to set identical threshold values for each channel which were used to feed the values needed for analyses in SMIA-CUKIE signifying positive labeled pixels.

SMIA-CUKIE usage and outputs. SMIA-CUKIE was written for the bulk analysis of high throughput acquired monochromatic images corresponding to the simultaneously labeled channels. See, Franco-Barraza et al., eLife, 2017 (6:e20600 DOI: 10.7554/eLife.20600).

Images were sorted in "Batch Folders" each containing the five monochromatic images corresponding to the original (unmixed) sample. The software (github.com/cukie/SMIA_CUKIE) was created to bulk process and analyze batches of monochromatic images providing localization (masks), intensities, and similar quantifying values (markers), including co-localizations of multichannel monochromatic immunofluorescent (or IHC, etc.) images. The software can identify intersection areas between an unlimited amount of masks while queried marker values and locations can also be estimated for numerous interrogations. The software requires identification of common nomenclatures to recognize each type of monochromatic image (vim for vimentin etc.) and necessitates information regarding the available number of masks and markers deposited in the batch folders containing the images (in our case there were three masks corresponding to nuclei, epithelium/tumor and stroma as well as two markers corresponding to adhesion structures and activated integrin). For each of the masks and markers the software requires a threshold number, which indicated the value (0-255) of pixel intensity that is to be considered positive for each channel (corresponding to each mask and marker). The software then allows choosing amongst all possible query combinations or provides an option for the user to write the desired tests to be queried. After running this function, the software rendered an excel file containing values of area coverage for the marker at the mask intersection (bona fide stroma) as well as total area coverage related to the image. Similarly, values included mean medium, standard deviation, total intensity and integrated intensities. The software's output includes the name of the folder batch each query is related to. In addition, the software can be instructed to provide image outputs corresponding to requested mask locations as well as markers shown solely at the corresponding mask intersections.

CRISPR/CAS9 mediated knockout (KO) of NetG1 in fibroblasts. Before performing CRISPR/Cas9 mediated knockout of NetG1, fibroblasts were immortalized with human telomerase (hTERT), using a retroviral infection with the pBABE-neo-hTERT vector, which was a gift from Robert Weinberg (Addgene plasmid #1774). First, to produce functional retrovirus, packaging cells Phoenix-Amphotropic (φNX) (ATCC #CRL-3213) at 50% confluence in 10 cm culture dishes were transfected with 10 µg of pBABE-neo-hTERT vector using 10 µL of Lipofectamine (Invitrogen, #18324) and 40 µL of Plus Reagent (Invitrogen, #11514015) in 6 mL of serum/antibiotics free Opti-MEM (Gibco, #31985062) culture media overnight at 37° C. in a cell culture incubator. The following morning, media was replaced with 10 mL of fresh Opti-MEM (serum/antibiotics free) and incubated 24 hours at 32° C. In the morning of days 2, 3 and 4 post-transfection, the conditioned media containing retrovirus was collected and filtered through a 0.45 µm syringe filter (Millipore, #SLHV013SL) and used for subsequent retroviral transfections of fibroblasts. For the viral infection, fibroblasts were cultured in 10 mL of conditioned media containing the retrovirus (supplemented with 4 µg/mL Polybrene (Santa Cruz, #sc-134220)) for 8 hours at 37° C. Then cells were washed and incubated with fresh culture media (DMEM 10% FBS, 1% L-Glut, 1% P/S) and incubated at 37° C. overnight. Beginning the next day, this infection procedure was repeated two additional times, for a total of three retroviral infections. Fibroblasts were then selected with G-418 at a concentration of 750 µg/mL until cells grew back to ~90% confluence. Cells were then expanded and tested for over-expression of hTERT, and lack of p16, by western blotting to confirm hTERT overexpression. These cells were used for CRIPSR/CAS9 mediated knockout of NetG1.

gRNA Design. To knockout the NetG1 encoding gene from fibroblasts, CRISPR/CAS9 gene editing was performed to introduce a frameshift mutation that disrupts the reading frame causing a premature stop codon to be read, ultimately halting translation and knocking out this gene.

First, gRNAs specific for NetG1 were designed using an MIT Optimized CRISPR Design website (crispr.mit.edu/) and the top two scoring gRNAs were selected, based on the presence of a PAM site (CAS9 recognition site) and limiting off-target binding. A non-targeting gRNA control was also designed.

Generation of Lentiviral KO Vector. Once the gRNA sequences were designed and ordered (Integrated DNA Technologies), they were cloned into the LentiCRISPR v2 vector (LentiCRISPR v2 was a gift from Feng Zhang; Addgene plasmid #52961). This is a dual-expression vector, expressing the CRISPR/CAS9 protein, as well as the cloned gRNA sequence driven by the human U6 promoter. Briefly, DNA oligos representing the gRNA sequences are listed below, with overhangs compatible with the Esp3I restriction enzyme (bold, underlined) and an additional G added to the beginning of each gRNA, with a complementary C on the reverse oligo (bold, italics), for efficient transcription driven by the human U6 promoter.

Next, the gRNA oligos stocks were diluted to 100 µM, and 1 µL of each gRNA pair was added to a T4 PNK reaction mixture (NEB, #M0201S) for a 10 µL reaction. The reaction was allowed to run in a thermal cycler to phosphorylate and anneal the oligos, according to the following program: 1) 37° C. for 30 minutes; 2) 95° C. for 5 minutes; and 3) Decrease 5° C. every minutes until 25° C.

To prepare the vector for cloning, 5 µg of LentiCrispr v2 vector were simultaneously cut with Fast Digest Esp3I (ThermoFisher, #FD0454) and dephosphorylated with Fast AP (ThermoFisher, #EF0651) for 30 minutes at 37° C. and subsequently run on a 1.5% agarose gel and purified for cloning using the GeneJet Gel Extraction Kit (Thermofisher, #K0691). To clone the annealed gRNA oligos into the vector, the oligos were diluted 1:200 in RNAase Free water (ThermoFisher, #4387937), and added to the quick ligation reaction mixture (NEB, #M2200S), along with 1 µL of the digested and dephosphorylated vector, and the reaction was carried out for 10 minutes at room temperature.

For bacterial transformation, 2 µL of the reaction was mixed with 50 µL of competent Stbl3 strain of *E. coli* for 30 minutes on ice. The bacteria were then heat shocked for 45 seconds at 42° C. and immediately transferred to ice for 2 minutes. Then 50 µL of the transformed bacteria were spread onto an LB/agar dish containing 100 µg/mL ampicillin and incubated at 37° C. overnight.

The next day, single colonies were screened by colony PCR using a U6 promoter forward primer and the corresponding reverse gRNA primers. Positive clones were selected to expand for plasmid purification and sequencing.

CRISPR Lentivirus Production. For functional Lentiviral production, viruses were generated in 293T cells using the cloned LentiCrispr v2 plasmids, and 2 packaging plasmids: psPAX (psPAX2 was a gift from Didier Trono; Addgene plasmid #12260), and VSVg. Briefly, 10 µg of cloned LentiCrispr V2, 5 µg of psPAX2, and 2 µg of VSVg were mixed in 1 mL serum-free/antibiotic-free DMEM in an 1.5 mL Eppendorf tube. 30 µL of X-treme Gene 9 (Roche, #06365787001) was added to the DNA mixture and gently mixed with the pipette tip. The mixture was allowed to sit for 45 minutes at room temperature. Next, the mixture was added drop-wise to a T75 flask containing 5 mL serum-free/antibiotic-free DMEM and 293T cells at ~85% confluence and slowly rocked for 30 seconds to evenly mix the DNA transfection mixture. The next morning, the serum free media was removed from the 293T cell flasks, and 10 mL of fresh DMEM containing 10% FBS and 1% penicillin/streptomycin were added to each flask. 2 days and 4 days post-transfection, the media was collected and filtered through a 0.45 µM syringe filter (Millipore, #SLHV013SL) and was used immediately for viral infection of target cells, or stored at −80° C. until needed.

CRISPR Lentiviral Infection. Target cells (naive or desmoplastic fibroblasts) were seeded at ~40% confluence in 2 mL complete fibroblast media in a 6 well plate. The following day, the target cells were infected with 2 mL of lentivirus for each corresponding CRISPR construct (eGFP or integrin gRNAs) in the presence of 10 µg/mL Polybrene (Santa Cruz, #sc-134220). As a control for the infection, cells were infected with a lentivirus overexpressing GFP, and the appearance of GFP-positive cells signified a successful infection. About 24 hours later, the media was replenished with fresh complete media for each cell type. After about 72 hours, puromycin selection (1 µg/mL for naive fibroblasts, 2 µg/mL for desmoplastic fibroblasts) of the infected cells began. The selection process lasted between 7-10 days; cells were expanded, and the efficiency of CRISPR/CAS9 knockout was assessed by western blotting. The cell lines with the greatest degree of target protein knockout were used for subsequent experiments.

Exosome Purification-Adapted from (Théry et. al. 2006):
1. Cells are plated and cultured to 90% confluence in T175 flask using full supplement media.
2. Once at 90% confluence, media is removed, cells are washed 2× with PBS, and 20 mL (per dish) Lipid Free Media (supplemented only with Penstrep if that is used in the full supplement media) is added to the cells.
3. Cells are incubated for 48 hours.
4. After media has been conditioned for 48 hours, it is collected in a conical tube and kept on ice.
   a. Care should be taken for the duration of the protocol to maintain the sample at our as close to +4° C. as possible to preserve the integrity of the exosome sample.
   b. The remaining cells should be lysed (according to standard Western Blot protocol) and collected for qualitative analysis in comparison to their excreted material.
5. The collected conditioned media (CM) is spun down at 300 g for 10 minutes to remove cells, cellular debris, and other contaminants. The resulting supernatant is transferred to a fresh conical tube (taking care to leave about 250-500 ul of liquid at the bottom of the tube to avoid transferring contaminants). This step is repeated once more but at a speed of 2000 g for 20 minutes.
6. After 2 mild spins, the supernatant is then filtered (under sterile conditions) through a 0.22 micron filter into a fresh conical tube.
7. We use an Ultracentrifuge rotor capable of spinning 8 mL maximum volume, so before that stage we must concentrate our CM using a centrifugal concentrator tube3. Before the filtered CM is then added to a Centrifugal Filter Unit, the Centrifuge filter must be primed with PBS. 5 mLs of PBS are added to the filter, and it is Spun down at 3200 g for 10-15 minutes or until most of the PBS has passed through the filter 8. The remaining PBS is discarded, and the filtered CM is then added to the primed Centrifugal Filter Unit to concentrate the media down in preparation for Ultracentrifugation.

The CM is spun down again 3200 g for about 30-40 minutes or until there the final volume of concentrated media is about 5-8 mL 9. The concentrated CM is then transferred to an Ultracentrifuge tube, inserted into its rotor adaptor, and weighed so that all samples/blanks are of equal weight to a hundredth of a gram.
   a. If samples are of unequal weight, add cold sterile PBS dropwise to the lighter sample.
10. The CM samples are then spun down in an Ultracentrifuge at 10,000 g for 45 minutes to pellet large EVs and contaminating organelles.
11. The supernatant is then transferred to clean Ultracentrifuge tubes and weighed for another spin.
   a. The remaining pellet can be collected and stored at −80° C. for future Western blot analysis.
12. The CM samples are then spun down in an Ultracentrifuge at 100,000 g for 2 hours.
13. Supernatant is CAREFULLY removed and stored at −80° C. Because the rotor model is swing bucket, the exosome pellet, which will appear invisible, will be directly at the middle of the bottom of the tube, thus avoid that area to prevent loss or destruction of your exosome sample.
14. 1 mL of sterile PBS is added to re-suspend and wash the exosome pellet, which is then spun down again at 100,000 g for 2 hours.
15. Supernatant is carefully removed, and the pellet is re-suspended in 40 ul of sterile PBS and transferred to a fresh micro-centrifuge tube. The purified exosome sample is now ready for further analysis.
   a. Samples should be aliquoted into individual samples and frozen at −80° C. for long term storage.
   b. If the assay being performed will benefit from the integrity of the vesicles (EM, IP, NTA), fresh samples are preferable to freeze-thawed.

Detecting/Scoring NetG1$^{(+)}$ EVs: Extracellular vesicles (EVs) that contain NetG1 can be named as NetG1$^{(+)}$ EVs. NetG1 EVs can be detected using Electron Microscopy (EM) or nanoparticle tracking analysis (NTA). For both techniques, EVs that have been isolated from CAFs are immune-labeled with an anti-NetG1 monoclonal antibody. Using EM this antibody is conjugated to a gold particle, and in NTA it is FITC-conjugated. In EM the labeled EVs are fixed to an EM grid and recorded at 60,000-135,000× magnification. EVs that have gold particles attached to them are distinguished as NetG1$^{(+)}$ EVs. In NTA, labeled EVs are diluted in PBS and pumped through a Nanosight (Malvern) machine. Software is set to record 3 60-second videos of particle flow, wherein the quantity and size of all particles recorded in the video is calculated. Using a FITC-channel filter, only particles/EVs that have been labeled will be measured. The quantity of these NetG1$^{(+)}$ EVs can then be compared against the total EV population and size distribution. To control for skews in size and/or concentration due to the antibody, recordings using EVs treated with a non-specific IgG1 FITC-conjugated antibody will also be used. Additionally, the antibody will be run without EV samples as a "blank."

Rescue PDAC Cells from Serum Starvation-Induced Cell Death Using CAF-Generated Conditioned Media Vs. CAF-Generated EVs:

Red fluorescent protein (RFP)-expressing kRAS/p53-transformed pancreatic epithelial cells were cultured using a 2% glutamine, 10% Fetal bovine-supplemented culture medium. 24 hrs before experimental conditions are implemented, full culture medium is switched to a glutamine-free, serum-free media. Extracellular vesicles (EVs) are collected using Differential Centrifugation (see above), and administered to the cells in serum-free media for 24 hours. After 24 hours, the cells are washed with PBS and treated with Sytox Green, a membrane-impermeable Fluorescent DNA-specific dye. Cells are incubated with Sytox Green for 30 minutes and then imaged on a Nikon confocal microscope. Cells are recorded at 10× magnification. Live cell count is measured in the TRITC (red) channel, and cell death is measured in the FITC (green) channel. Raw images are adjusted in Photoshop to create black/white thresholds capable of being quantified using ImageJ software. PDAC cell death count is acquired as the average of the area of live cells (red) divided by area of cell death (green) per image. Data is compiled by averaging the results of three-technical replicates, consisting of 13-18 sets of pictures per replicate.

Example 2: Upregulation of NetG1 in CAFs and Upregulation of NGL1 in PDAC

By combining the 3D stroma approach with screening (via Agilent's 44,000 genes) of mRNA expression obtained from two patient-matched normal stroma (n) and detrimental PDAC desmoplasia (t), significant overexpression of pre-synaptic and neural synapse maintenance protein NetrinG1 (NetG1 or NG1) and of its recently recognized splice regulator, neuro oncological ventral antigen-1 (NOVA1) was observed. Analysis by the Fox Chase Biostatistics facility identified 36 unique genes (red and green are high and low expressions, respectively; n and t indicate normal and tumor-allied samples, respectively) with p-value less than 1% and minimum 2-fold changes in expression. NG1 and NOVA1 genes were up-regulated by 8.2-fold and 5.8-fold in D-ECM producing CAFs (compared to normal) and showed low probability of being identified by chance (P=0.001 and P=0.003), respectively. These two molecules, together with additional known pancreatic desmoplastic biomarkers such as Caveolin-1 (Cav1) and others were validated at both RNA and protein levels.

Referring to FIG. 1 (panel A), a microarray was carried out and demonstrated upregulation of NetG1 in CAFs compared to normal patient matched fibroblasts confirmed at the mRNA and protein levels. Gels include NG1 mRNA and protein levels while graphs correspond to qRT-PCR and densitometry measurements relative to loading controls and as indicated in the corresponding Y axes. U87 brain cell lysates served as NetG1 positive control. A series of blots was carried out comparing 4 primary normal pancreatic stellate cells and 5 primary CAFs, derived from PDAC patients, with normal fibroblasts generally expressing less NetG1. Referring to FIG. 1 (panel B), immunofluorescence corresponds to patient original surgical samples and depict 5-color Simultaneous Multi-channel Immunofluorescence of stroma (stro), epithelium (epi) and nuclei (nuc) with NetG1 (G1), NOVA1 and Peg10 bio-markers. Right panels are the monochromatic images of the tumoral (high in stroma) markers. Referring to FIG. 1 (panel C), blots were performed and demonstrated that NGL1 was upregulated in PDAC cells (KRAS) and in different PDX cell lines obtained from PDAC patients. Referring to FIG. 1 (panel D), analysis comparing 4 normal pancreata and 15 PDAC patient tissue samples show increased expression of NG1 and p-FAK in the stroma of PDAC patients, as well as a positive correlation between the expression of NetG1 in the stroma and NGL-1 in the tumor compartment.

Figure 2:
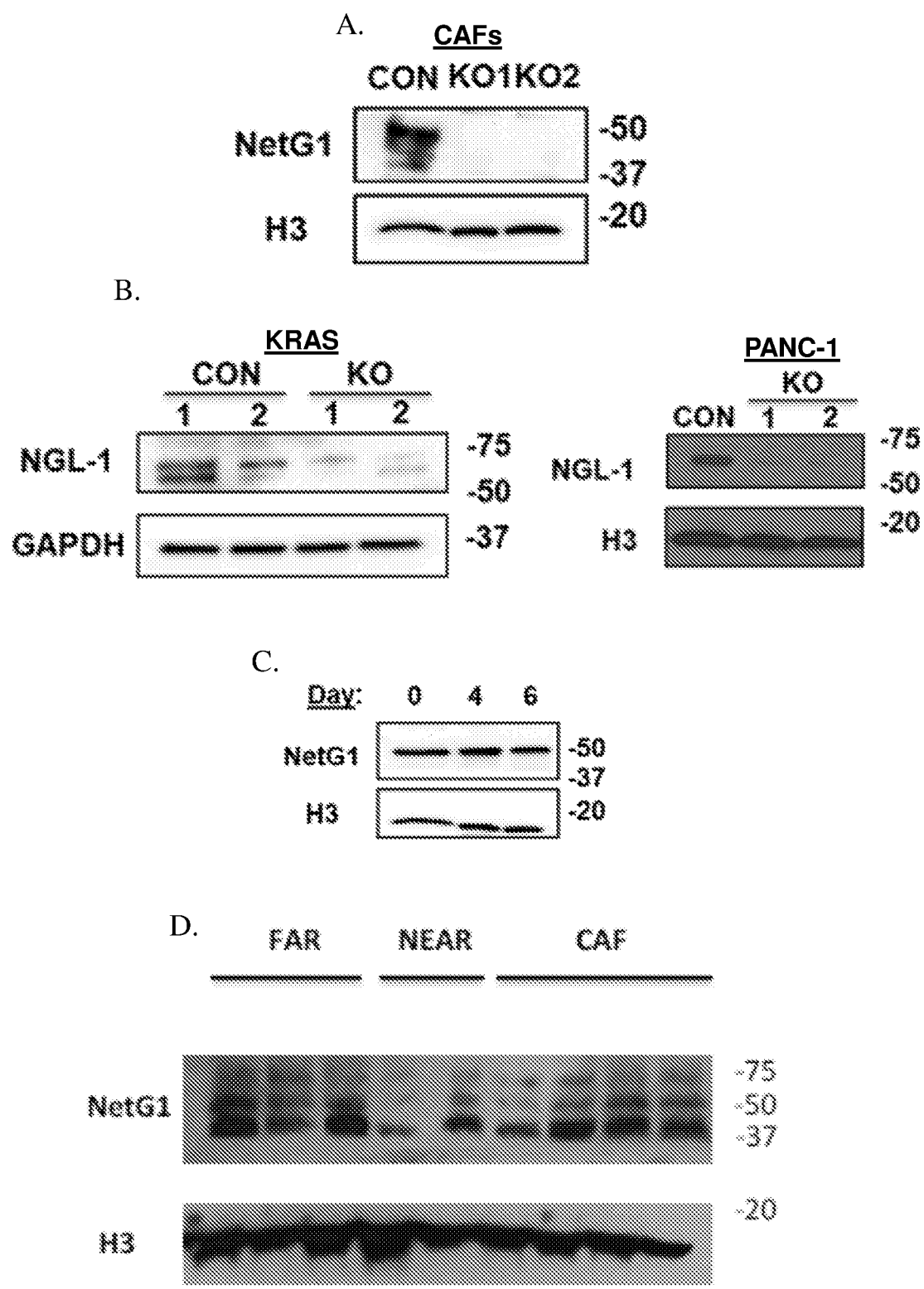
FIG. 2 (panels A, B, C, and D) NetG1 and NGL1 were knocked out using CRISPR/Cas9 in CAFs and PDAC cells, respectively. Expression of NetG1 is maintained during 3D matrix production and its expression was detected in fibroblasts at different distances from the tumor border in a PDAC patient sample.

To better understand the role of NetG1 and NGL1, these were knocked out in CAFs and PDAC cells, respectively, using CRISPR/Cas9. Referring to FIG. 2 (panel A), knockout of NetG1 was performed in CAFs. Referring to FIG. 2 (panel B) knockout of NGL1 was demonstrated in PDAC cell lines (KRAS and PANC-1). Referring to FIG. 2 (panel C) NetG1 expression was maintained through 3D matrix production. Referring to FIG. 2 (panel D), a patient fibroblast panel demonstrated NetG1 expression in all CAFs tested.

Example 3: Knockout of NetG1 in CAFs or NGL1 in PDAC

Figure 3:
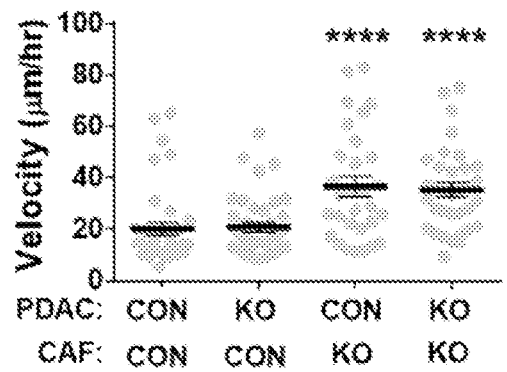
FIG. 3 (panels A, B, and C) show that knockout of NetG1 in CAFs or NGL1 in PDAC results in decreased interactions between CAFs and PDAC.
Figure 3:
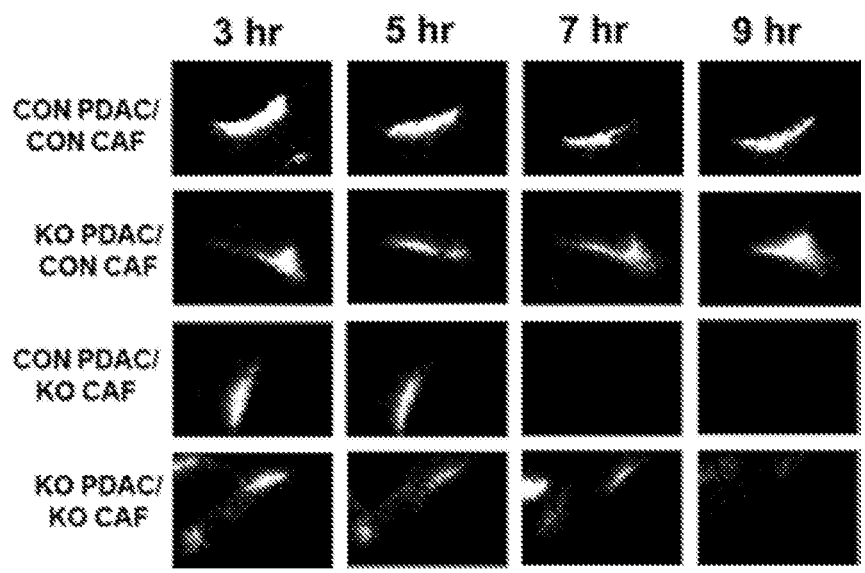
Figure 3:
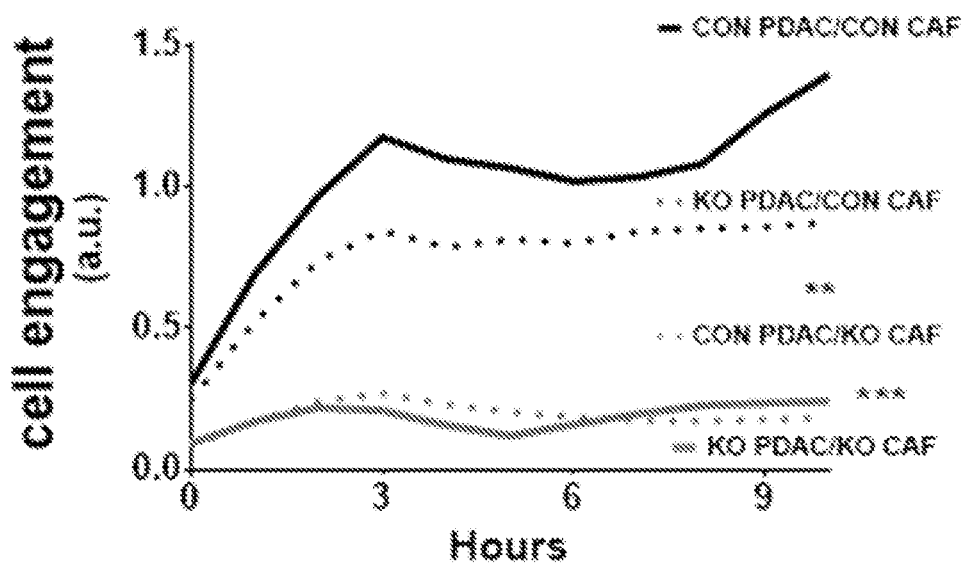
Figure 3:
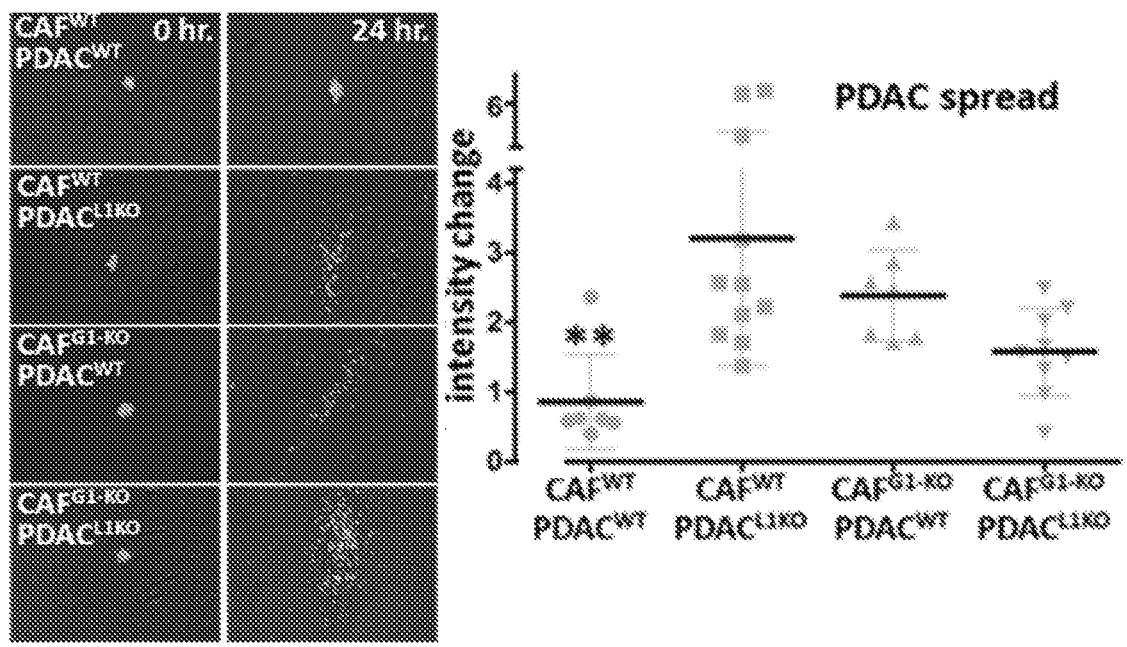

Knockout of NetG1 in CAFs, or NGL1 in PDAC, resulted in decreased interactions between CAFs and PDAC. Referring to FIG. 3 (panel A), when CAFs and PDAC were allowed to interact for 24 hours and in conditions where CAFs lacked NetG1, or PDAC lacked NGL1, PDAC cells moved significantly more. Referring to FIG. 3 (panel B), black and white images of areas of interaction between PDAC and CAFs were obtained during 9 hours, and demonstrated that when NGL1 or NetG1 is knocked out, PDAC-CAF interactions are reduced. Referring to FIG. 3 (panel C), spheres of PDAC (CON or NGL1 knockout) were placed on a bed of CAFs (CON or NetG1 knockout). Spheres of CON PDAC remained contained, whereas any knockout condition sphere moved 2-3 times further, indicating that NetG1/NGL1 mediated PDAC-CAF interactions.

Figure 4:
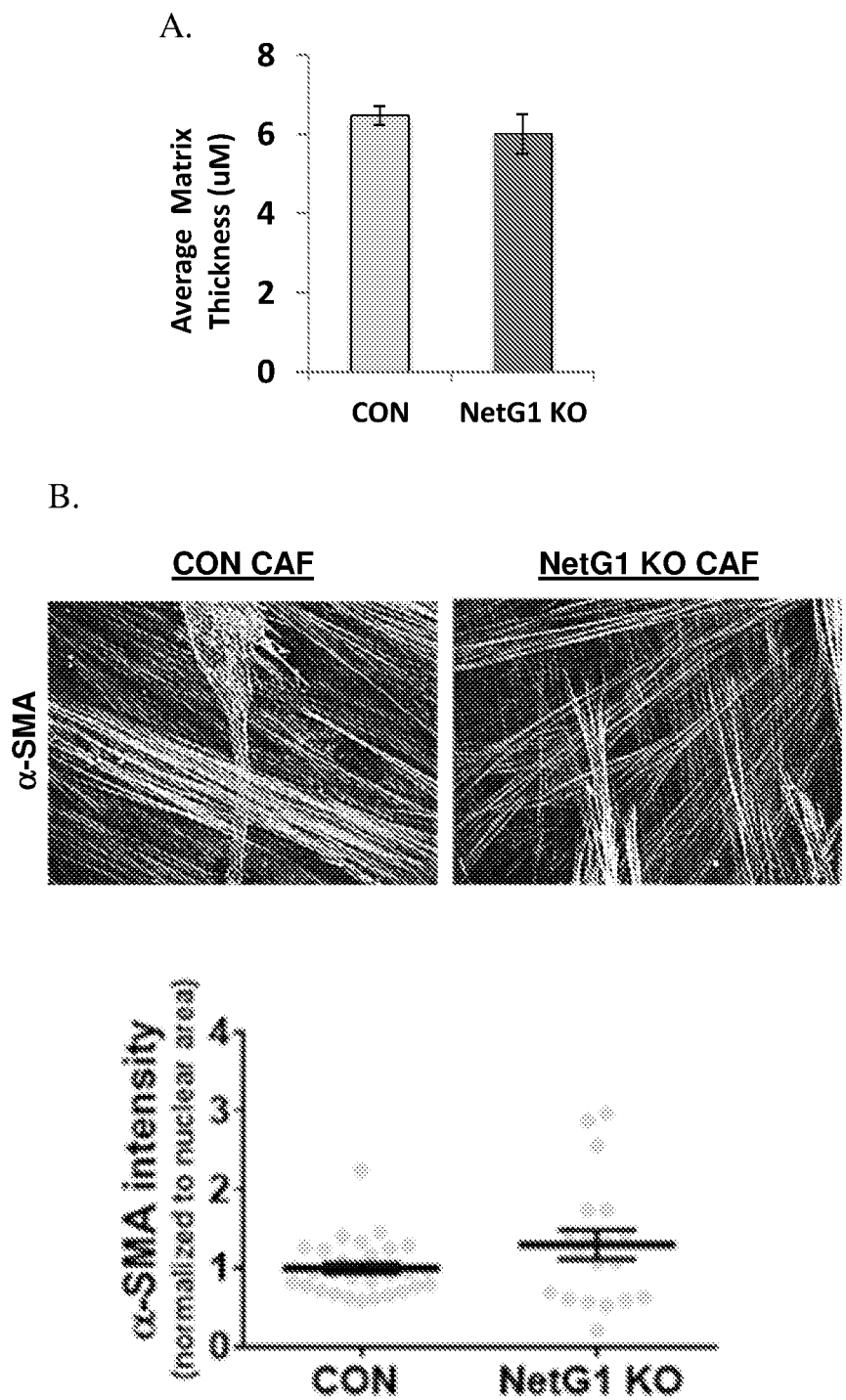
FIG. 4 (panels A, B, C, and D) show that knockout of NetG1 does not significantly alter the CAF phenotype during matrix production but that levels of active α5β1 and p-FAK were lower in the NetG1 knockout CAFs, suggesting their function is anti-tumorigenic despite of the classic traits.
Figure 4:
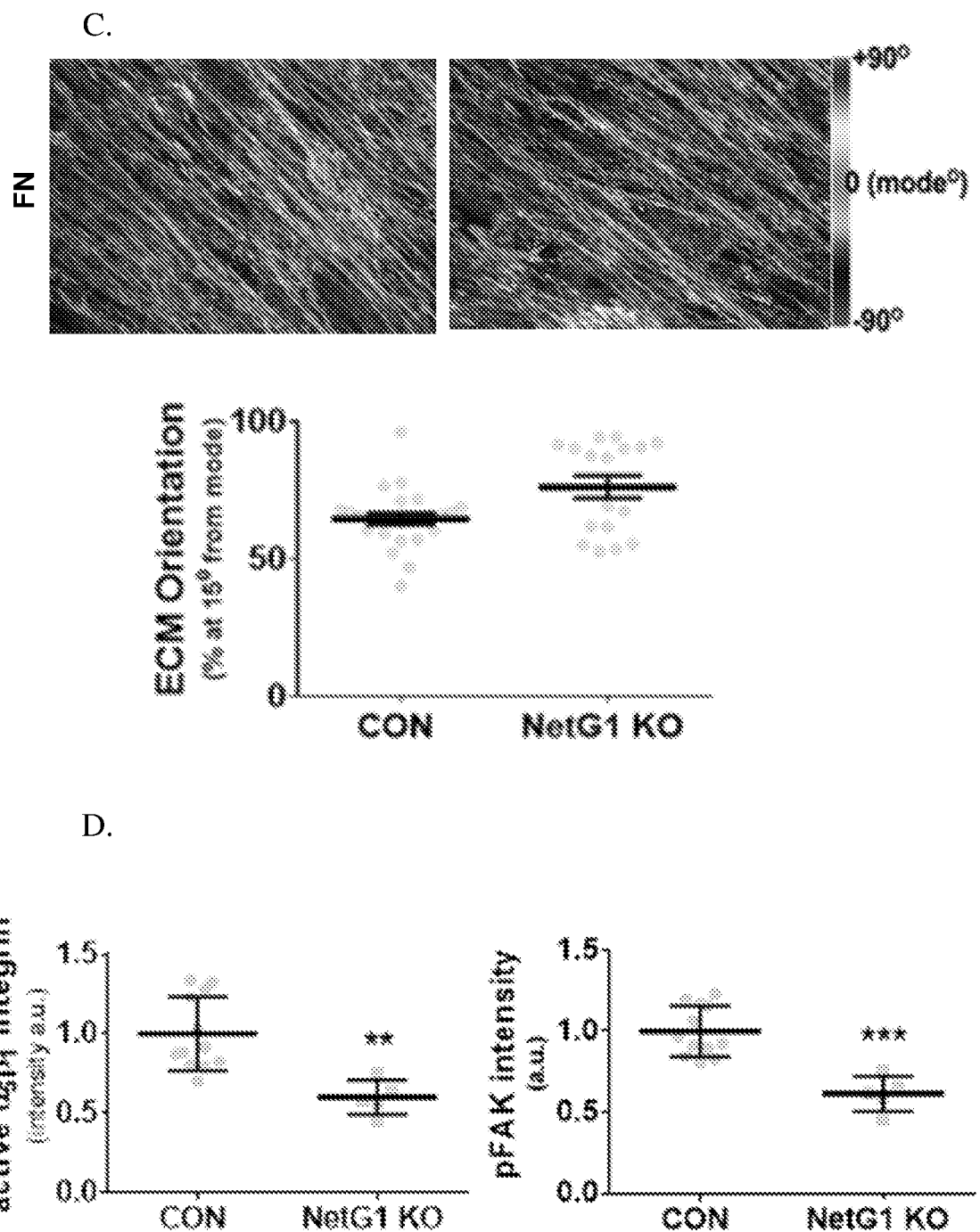

Knockout of NetG1 did not significantly alter the CAF phenotype during matrix production. Referring to FIG. 4 (panel A), the extracellular matrix (ECM) thickness was not altered by knockout of NetG1. Referring to FIG. 4 (panel B), smooth muscle actin intensity was unchanged in NetG1 knockout CAFs. Referring to FIG. 4 (panel C), ECM alignment was demonstrated to be similar between CON and knockout CAFs. Referring to FIG. 4 (panel D), levels of active 501 and p-FAK were lower in the NetG1 knockout CAFs.

Example 4: Interaction of CAFs and PDACs

Figure 5:
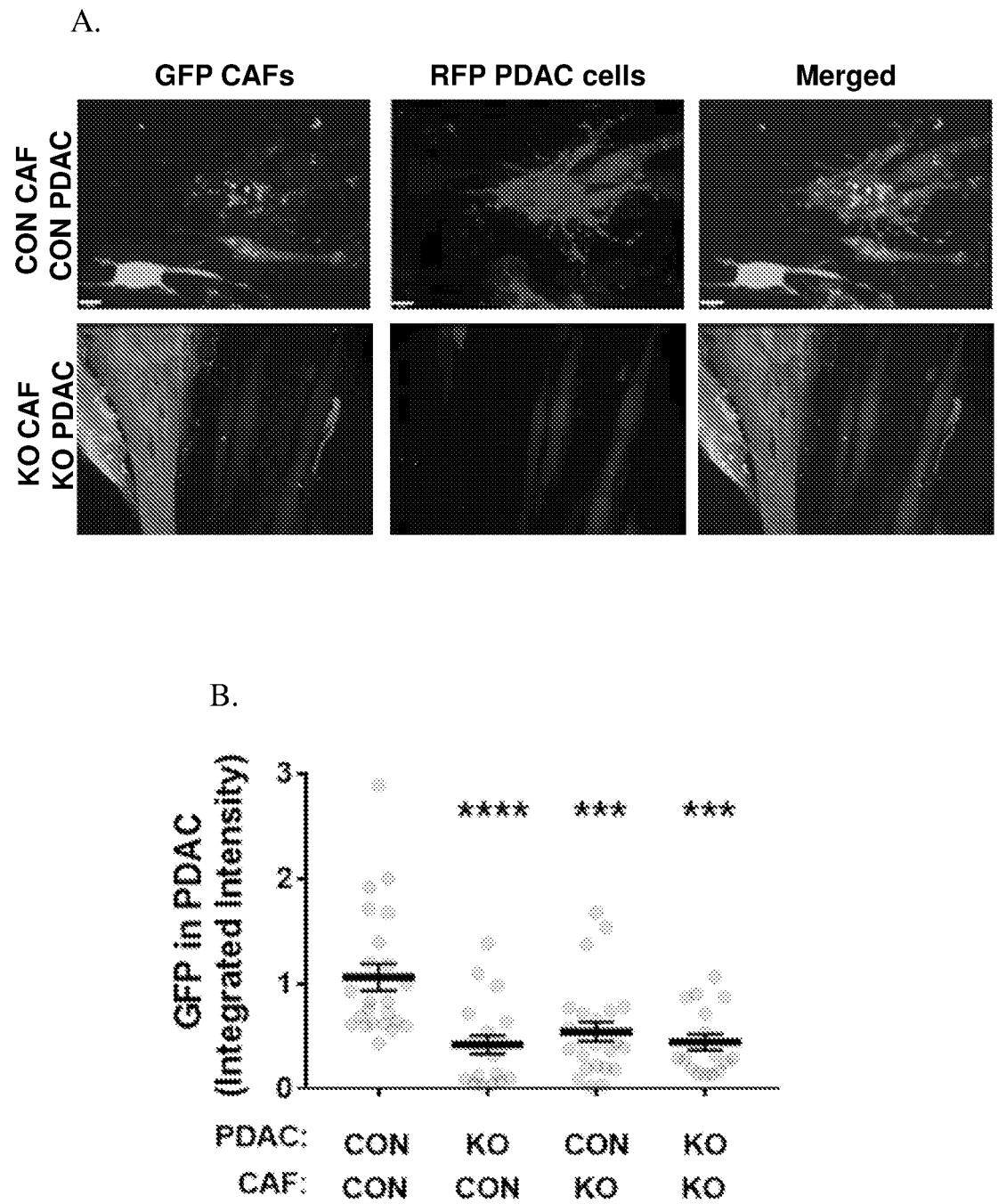
FIG. 5 (panels A, B, and C) show that CAFs transfer material to PDAC cells in a NetG1/NGL1-dependent manner.
Figure 5:
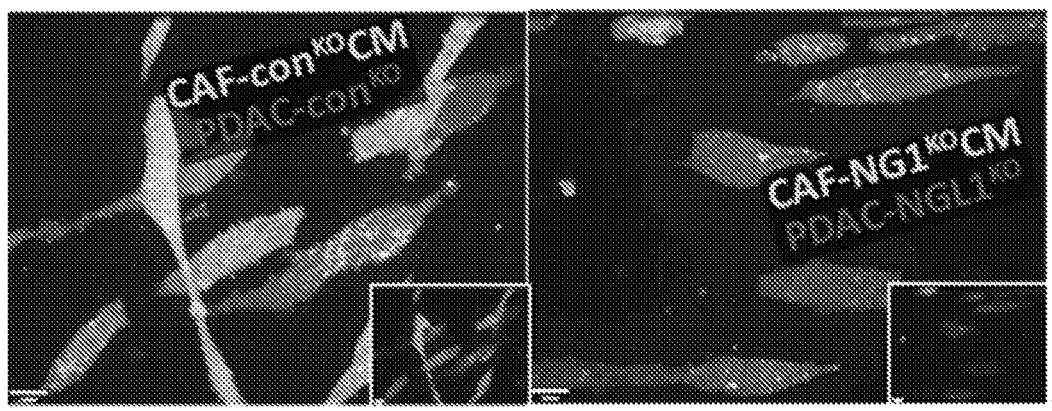
Figure 5:
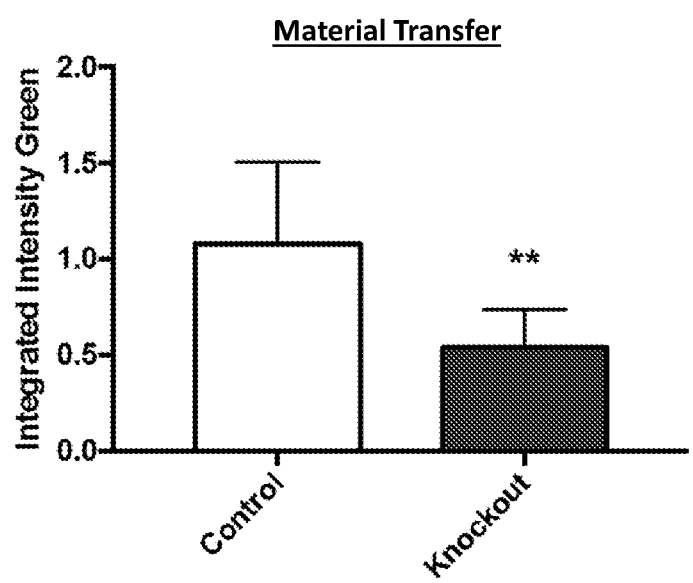

Referring to FIG. 5 (panel A), representative confocal images were obtained that depicted GFP transfer in CON CAF/CON PDAC co-culture, but not in knockout/knockout co-culture. Referring to FIG. 5 (panel B), shows the results of quantification of a material transfer assay. Referring to FIG. 5 (panel C), a material transfer assay was carried out with conditioned media from CAFs, demonstrating that less material was transferred to PDAC in knockout conditions.

Figure 6:
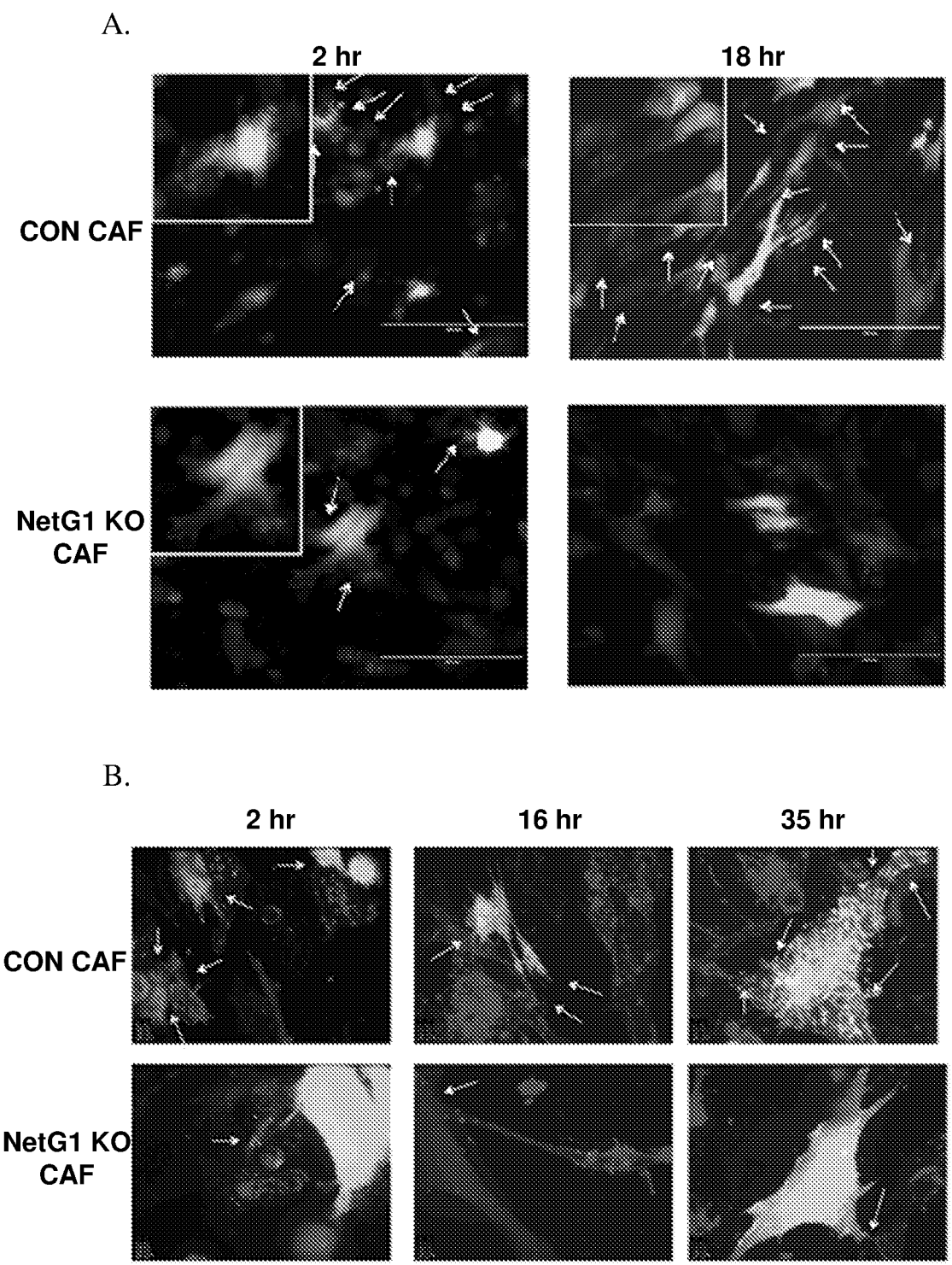
FIG. 6 (panels A and B) show that CAFs and PDAC interact, dependent on NetG1 in CAFs.

CAFs and PDAC interaction was demonstrated to be dependent on NetG1 in CAFs. Referring to FIG. 6 (panels A and B), it was demonstrated that NetG1 in CAFs was involved in CAF-PDAC cell engagement.

Example 5: Support of PDAC Survival by CAFs

Figure 7:
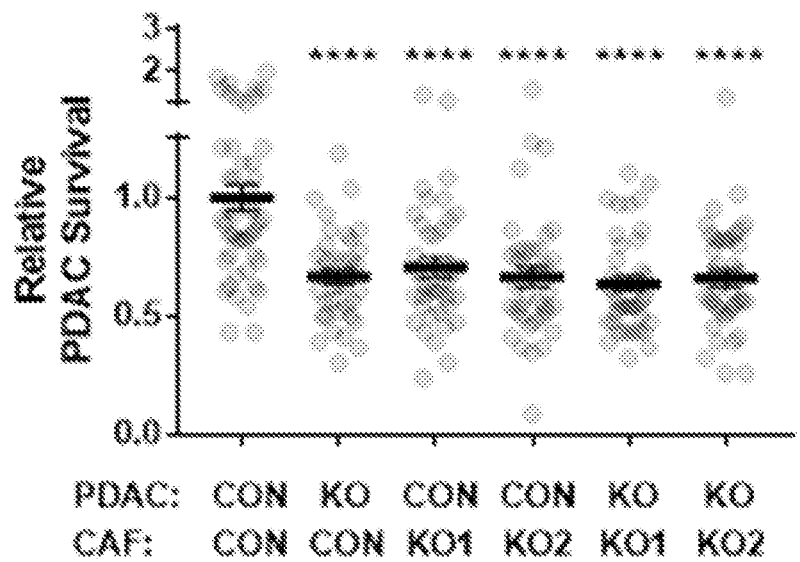
FIG. 7 (panels A, B, C, D and E) show that CAFs and their extracellular matrices support PDAC survival in stressful conditions (e.g., serum free, glutamine free) in a NetG1/NGL1-dependent manner and that the production and transport of glutamine and glutamate is impaired in NetG1 and NGL-1 knockout cells. Observe the partial rescue of PDAC survival when Glutamine or Glutamate is added back to the culture conditions (panel D).
Figure 7:
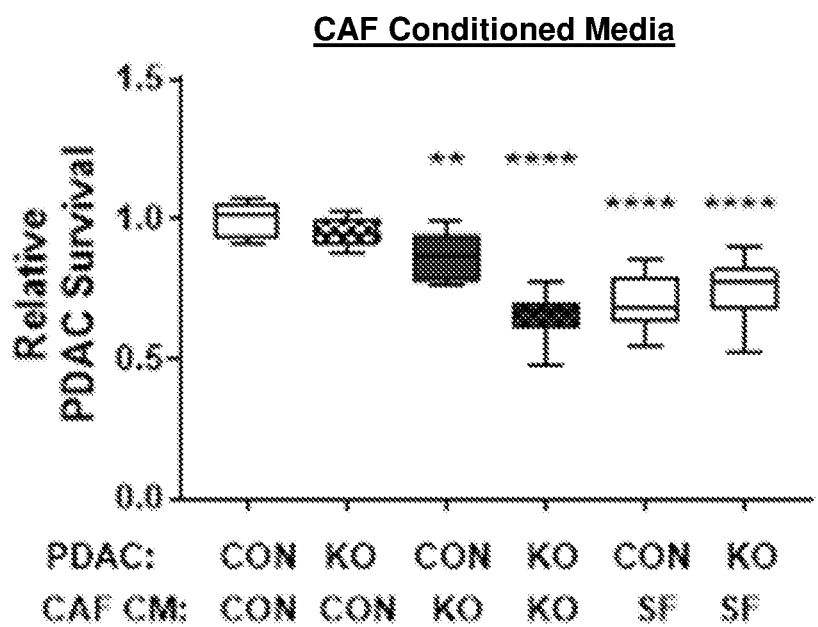
Figure 7:
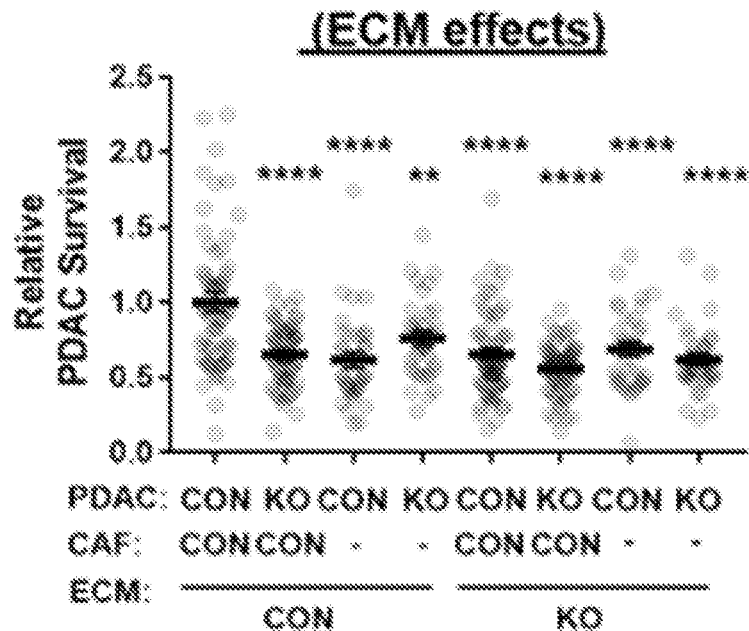
Figure 7:
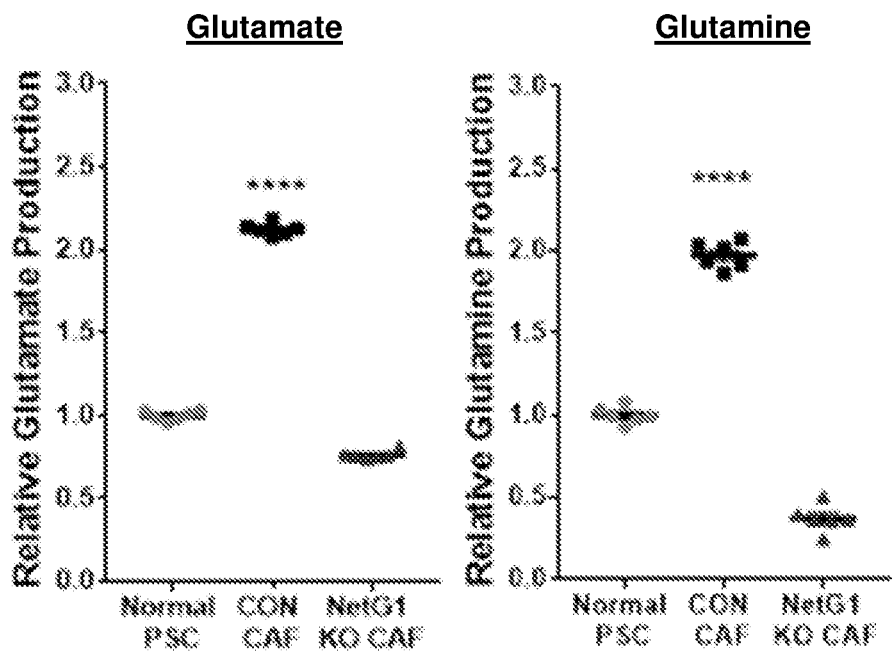
Figure 7:
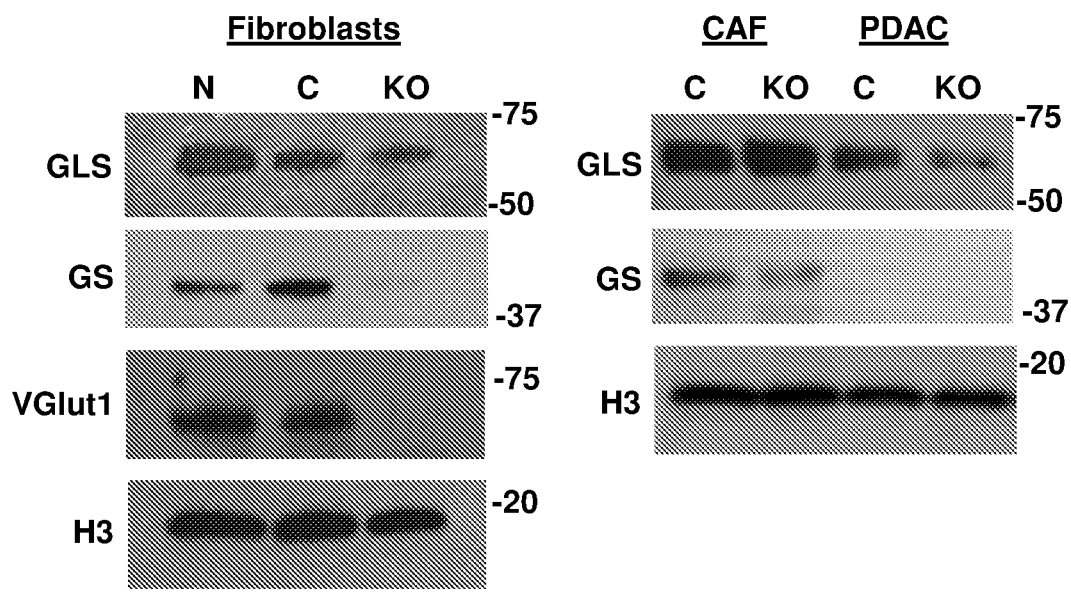
Figure 7:
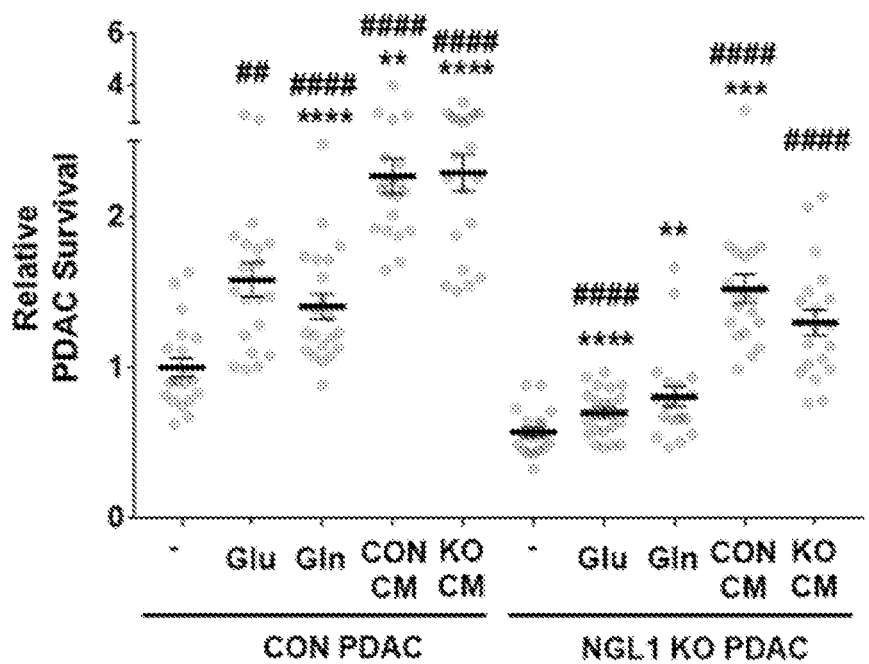

CAFs and their derived extracellular matrices were demonstrated to support PDAC survival in stressful conditions (serum free, glutamine free) in a NetG1/NGL1-dependent manner. Referring to FIG. 7 (panel A), knockout of NetG1 in CAFs did not support PDAC survival. Referring to FIG. 7 (panel B), extracellular matrix produced by NetG1 knockout CAFs is less supportive to PDAC survival. Referring to FIG. 7 (panel C), knockout of NetG1 in CAFs produced less glutamate and glutamine. Referring to FIG. 7 (panel D), knockout of NetG1 in CAFs and knockout of NGL1 in PDAC expressed less glutamine/glutamate related proteins. Referring to FIG. 7 (panel E), adding back glutamine and glutamate to the stressful culture conditions partially rescued PDAC survival.

Figure 8:
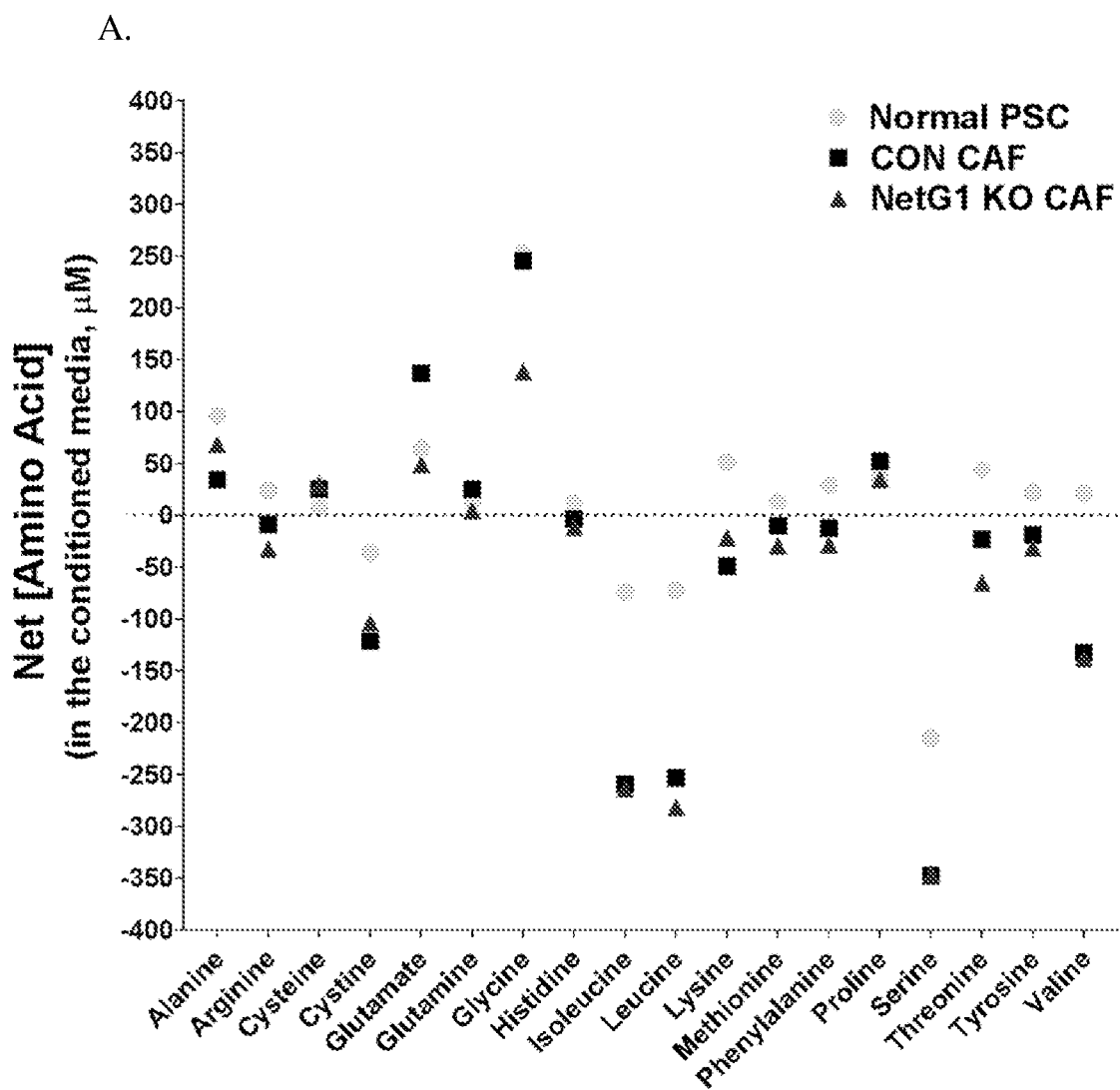
FIG. 8 (panels A and B) shows amino acid screening in normal fibroblasts and CAFs (CON and NetG1) and that knockout of NetG1 alters the production of numerous amino acids.
Figure 8:
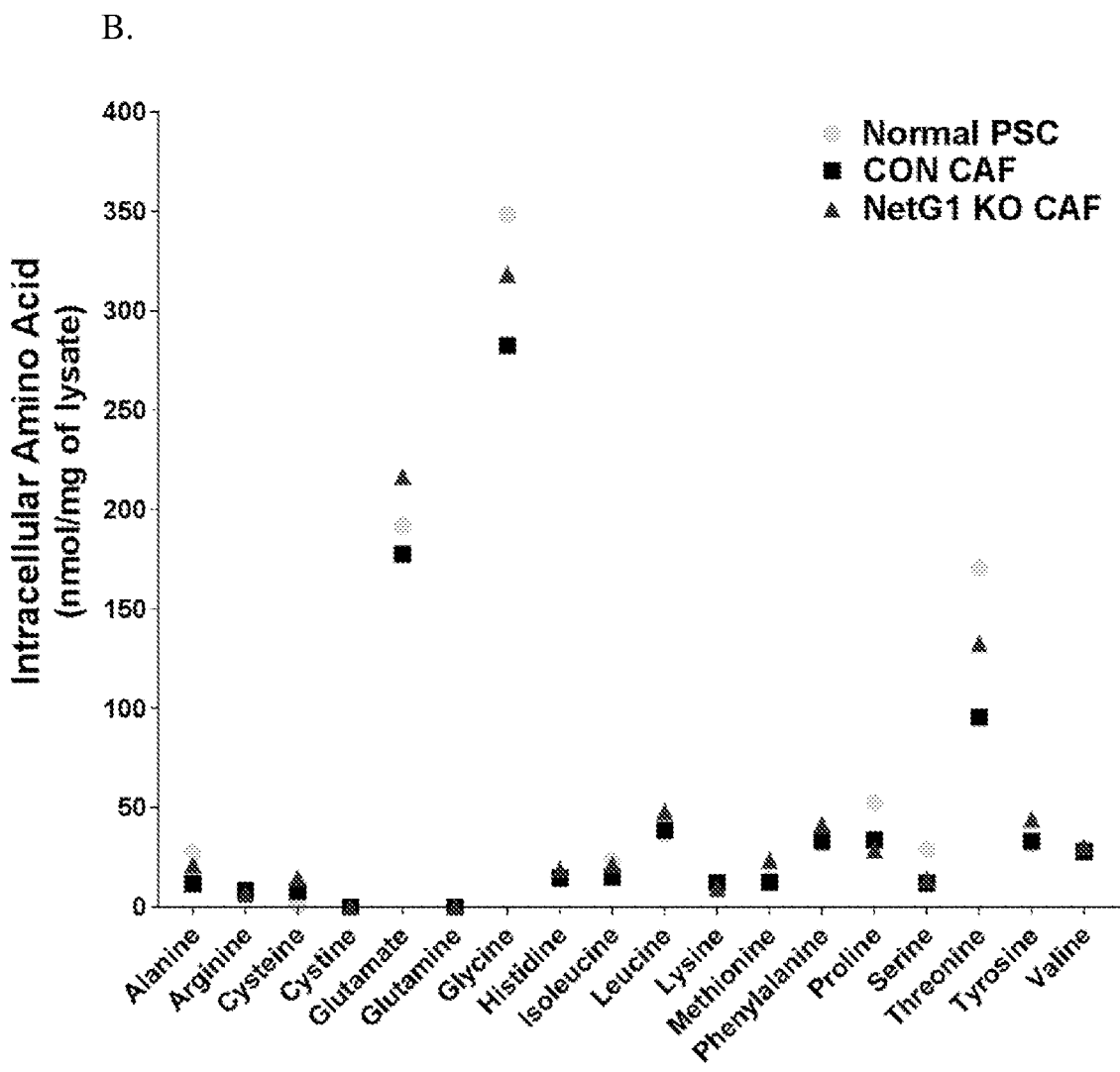

Referring to FIG. 8, amino acid screening was carried out in normal fibroblasts and CAFs (CON and NetG1) and demonstrated that knockout of NetG1 altered the production of many amino acids.

Example 6: NGL1 Expression in PDAC and Cell Death

Figure 9:
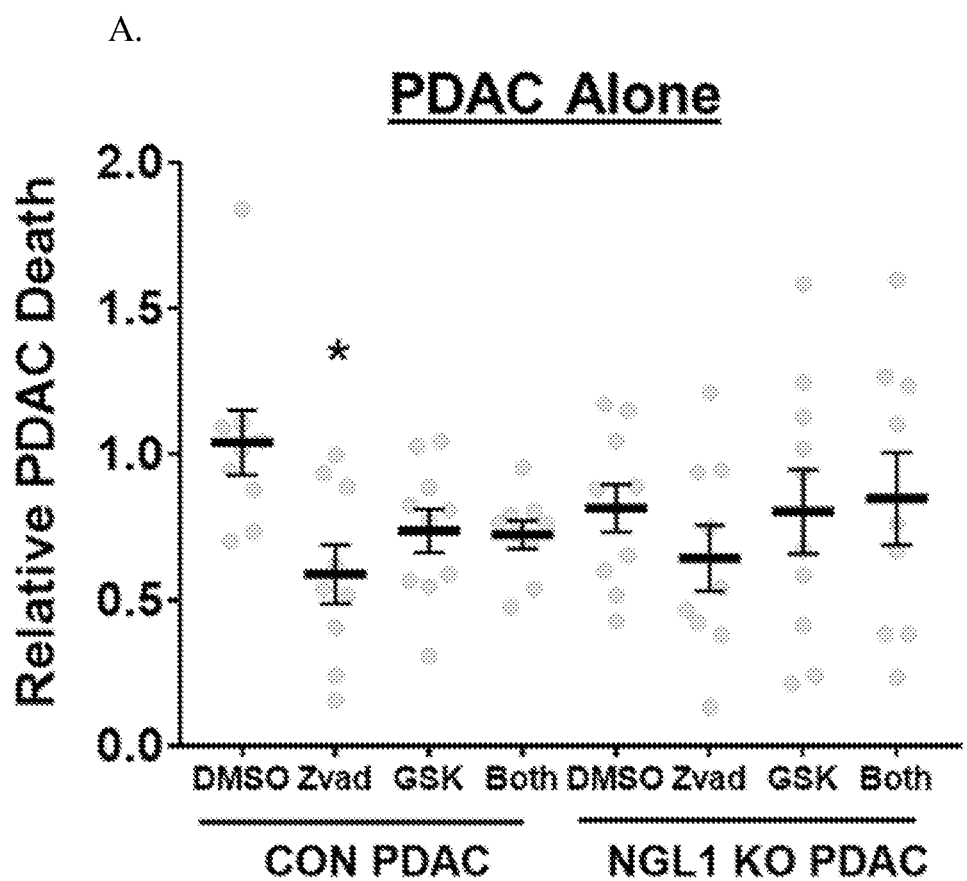
FIG. 9 (panels A and B) show that NGL1 expression in PDAC determines the mode of cell death under stressful co-culture conditions with CAFs.
Figure 9:
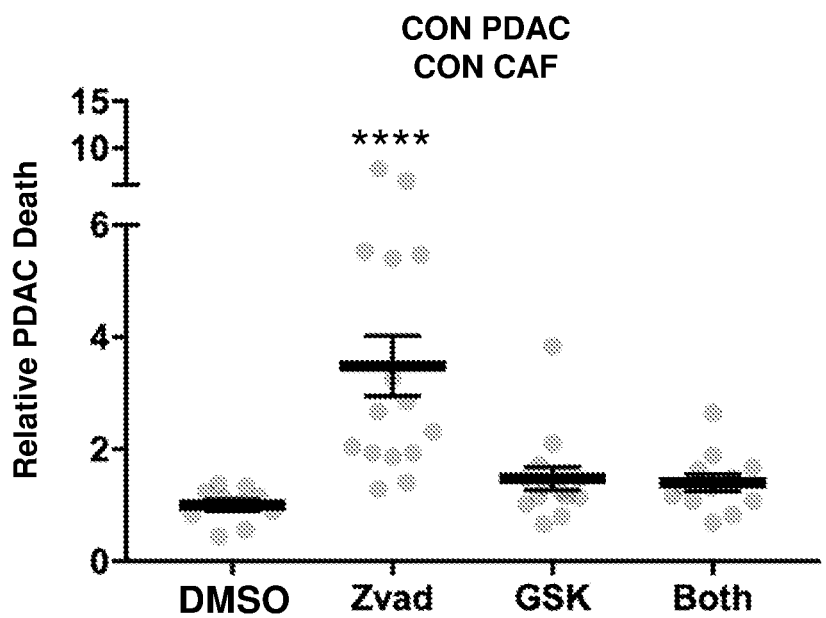
Figure 9:
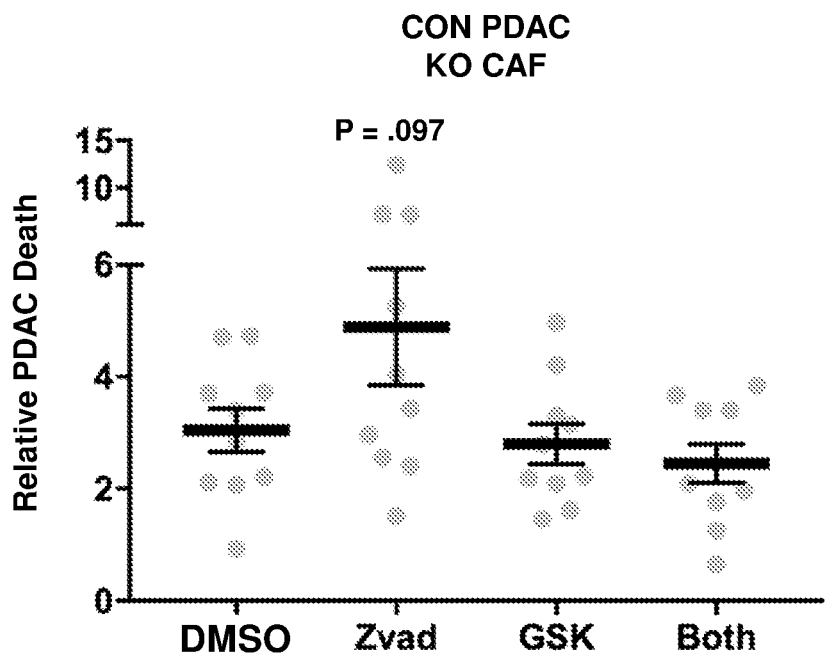
Figure 9:
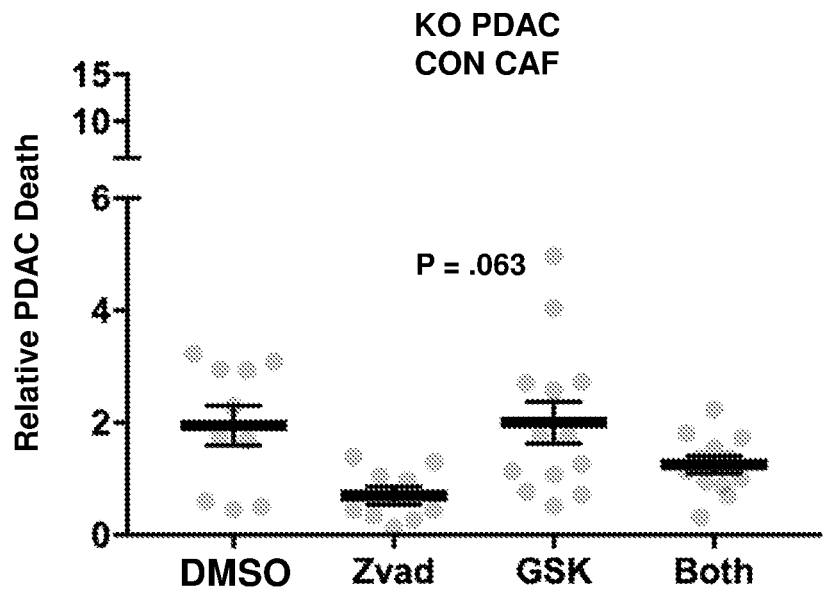
Figure 9:
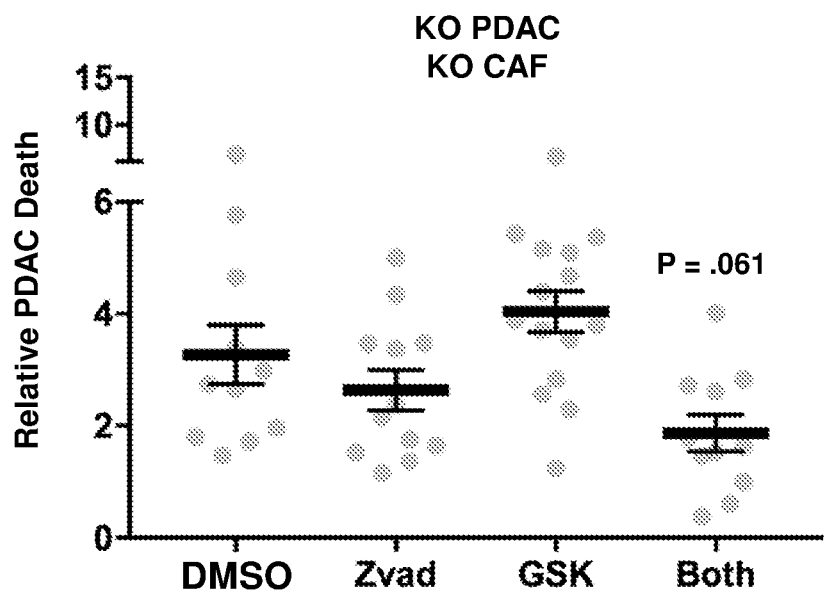

NGL1 expression in PDAC determined the mode of cell death under stressful co-culture conditions with CAFs. Referring to FIG. 9 (panel A), cell death quantification of PDAC (CON or knockout) cultured alone in 3D was carried out. Referring to FIG. 9 (panel B), cell death quantification of PDAC (CON or knockout) co-cultured with CAFs (CON or knockout) in 3D was also carried out. NGL1$^+$ PDAC were driven to necroptotic death by caspase inhibiton (zvad), while NGL$^-$ PDAC were protected from death by caspase inhibition. Also, knockout of NetG1 I CAFs drove PDAC to higher amounts of death across all conditions.

Figure 10:
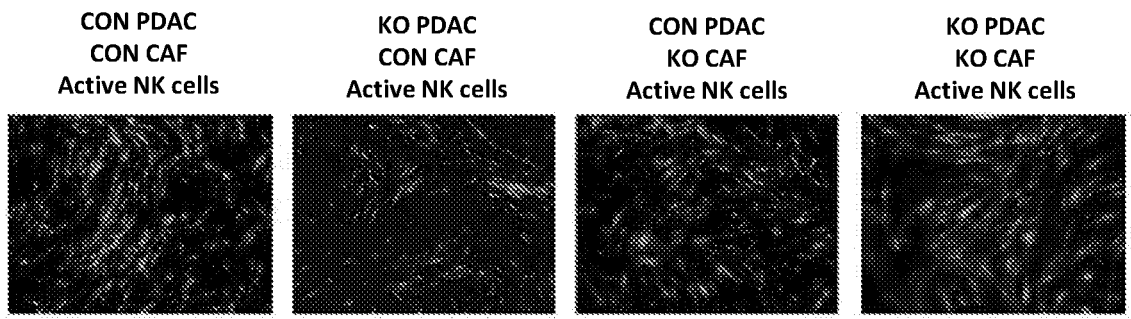
FIG. 10 (panels A, B, C, D, E, F, and G) show that knockout of NetG1 in CAFs support NK cell killing of PDAC in multiple in vitro models.
Figure 10:
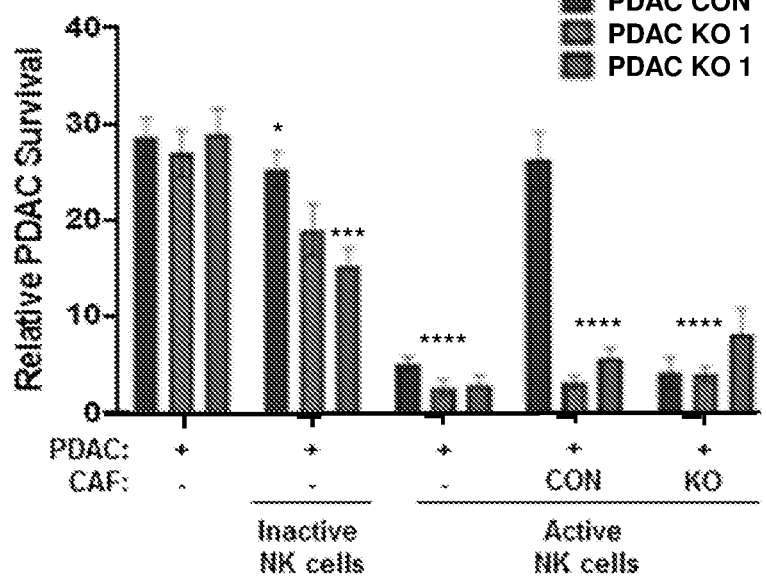
Figure 10:
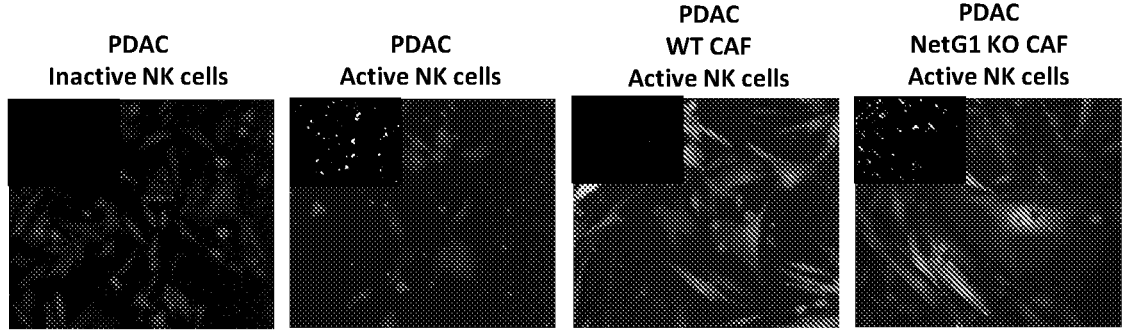
Figure 10:
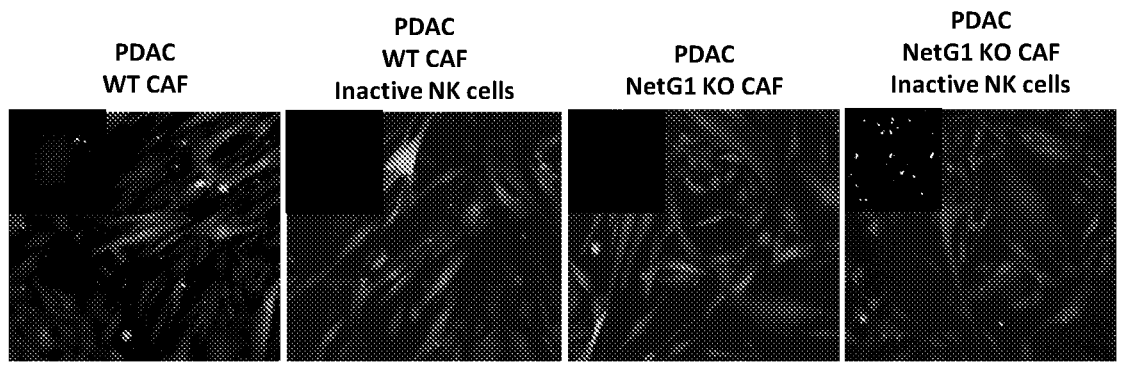
Figure 10:
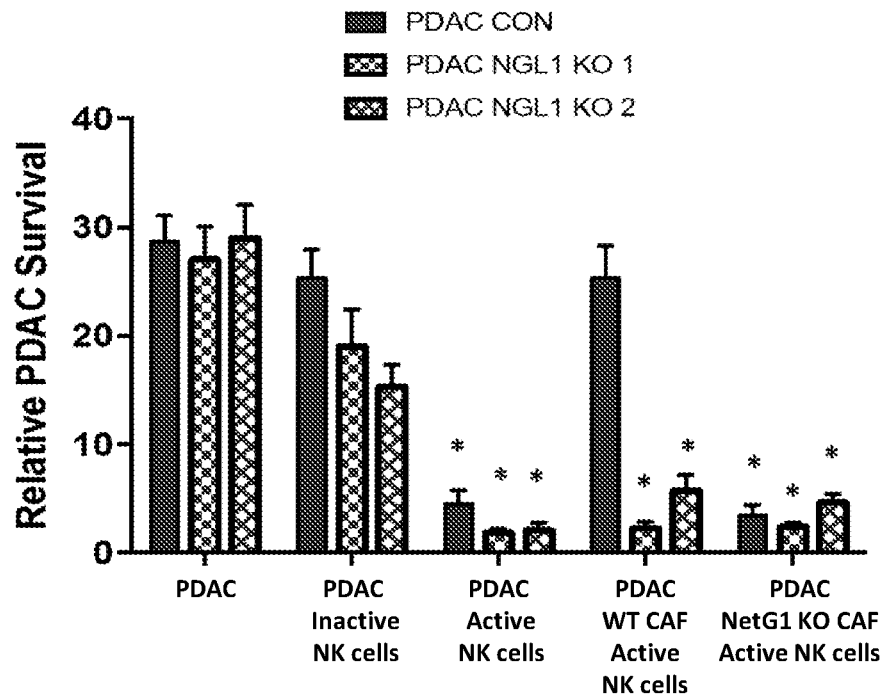
Figure 10:
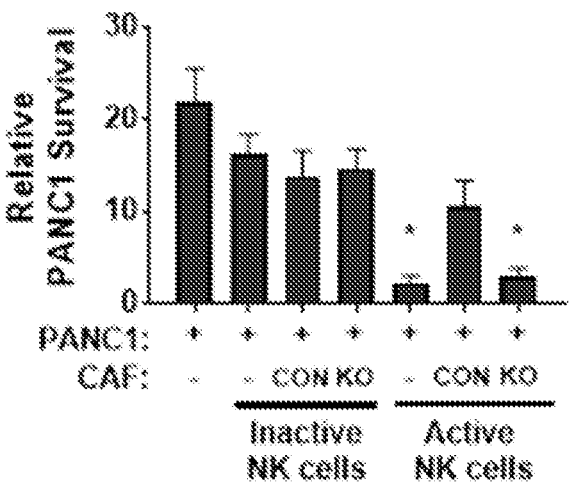
Figure 10:
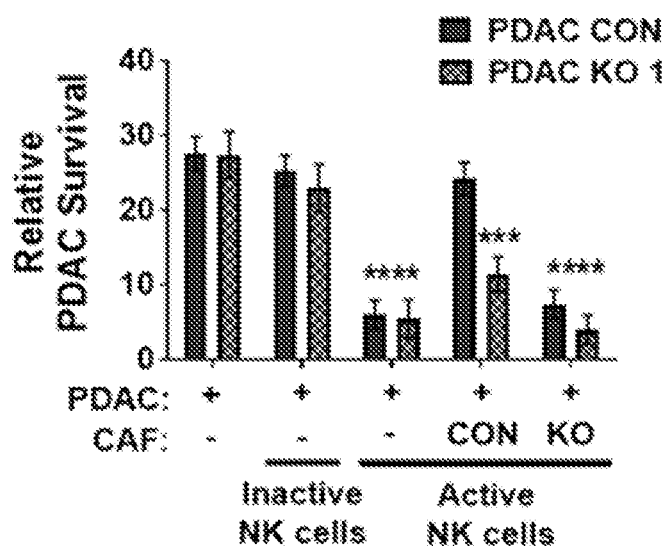
Figure 10:
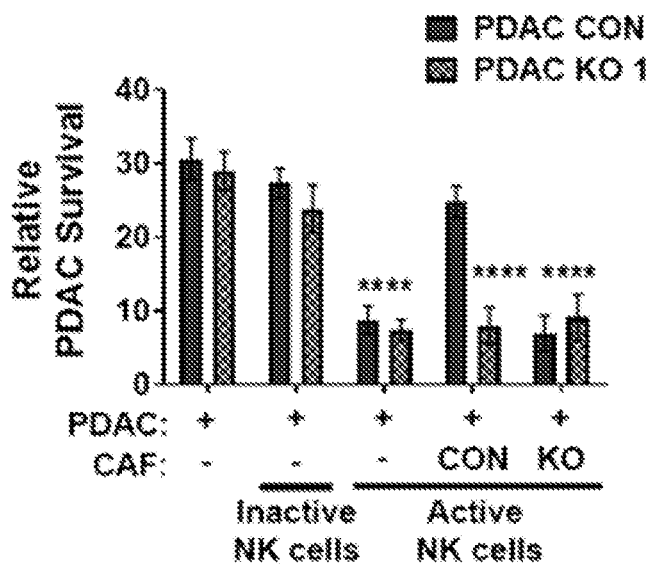
Figure 10:
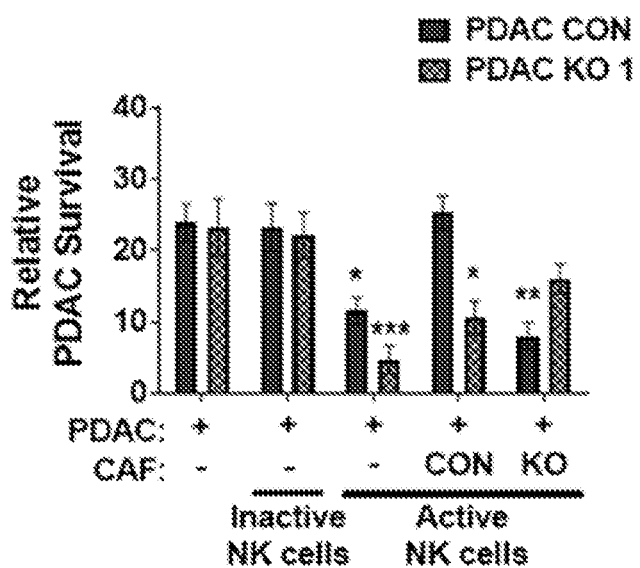

Knockout of NetG1 in CAFs supported NK cell killing of PDAC in multiple in vitro models. Referring to FIG. 10 (panel A), representative images of 3D NK cell assay were obtained. Referring to FIG. 10 (panel B), the same NK cell assay was performed in 2D (on plastic culture dish) and demonstrated NetG1/NGL1-dependent killing of PDAC by NK cells. Referring to FIG. 10 (panel C), representative images of 2D NK cell assay were obtained. Referring to FIG. 10 (panel D), representative images of 3D NK cell assay were obtained. Referring to FIG. 10 (panel E), an alternative method to activate NK cells was performed, and yielded the same results (CAFs protected PDAC from NK cell-induced death in a NetG1/NGL1-dependent manner). Referring to FIG. 10 (panel F), knockout of NetG1 in CAFS using a different PDAC cell line (PANC-1) yielded the same results (i.e., no PDAC protection from NK cell-induced death). Referring to FIG. 10 (panel G), different ratios of CAFs:PDAC were used in an NK cell assay, and resulted in the same trend.

Figure 11:
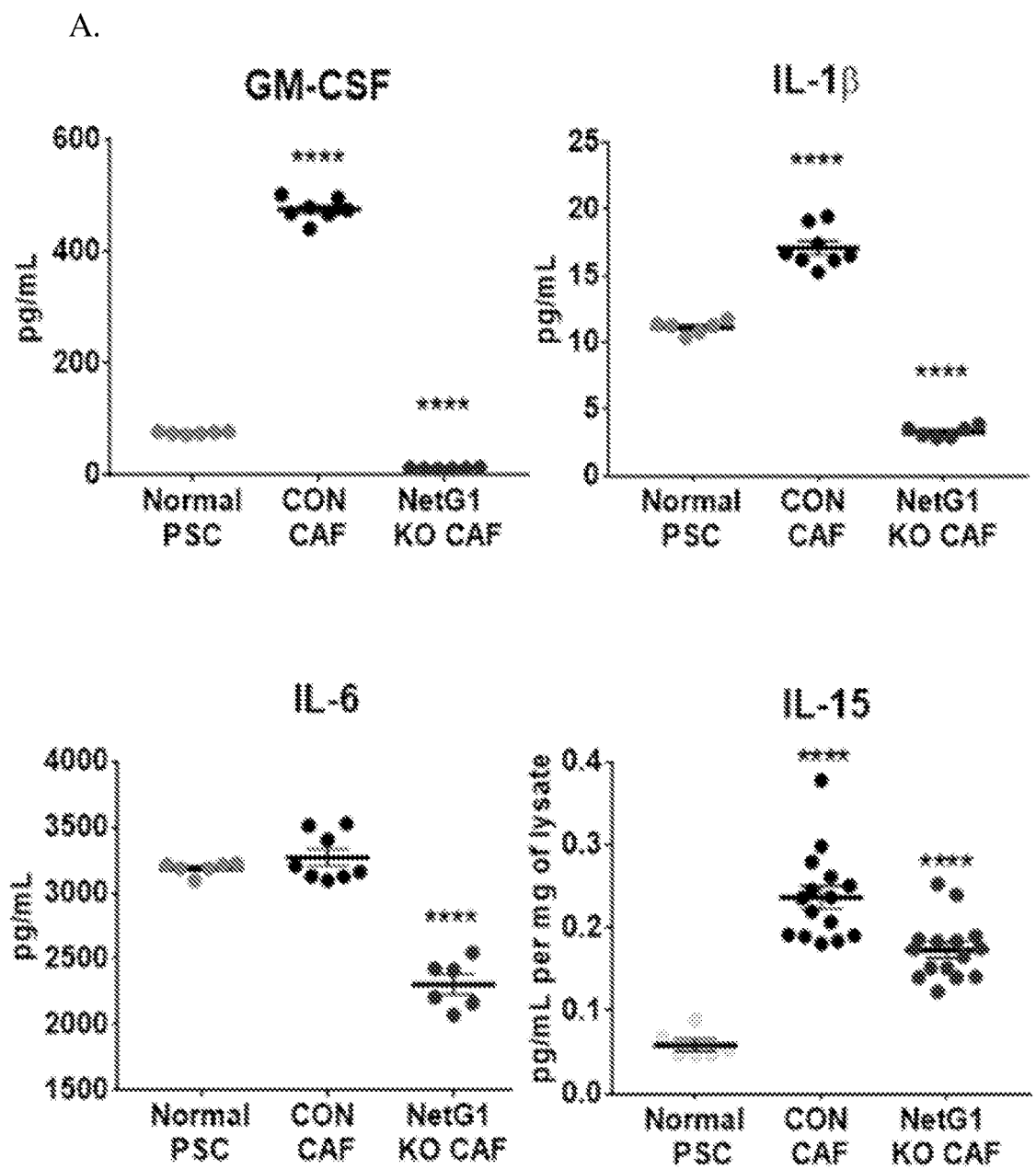
FIG. 11 (panels A, B, C, D and E) show that knockout of NetG1 in CAFs reduces immunosuppressive cytokine secretion, and CAFs impair NK cells cytotoxic function, protecting PDAC from NK cell induced death, in a NetG1/NGL1-dependent manner in a process partially regulated by glutamate and IL-15.
Figure 11:
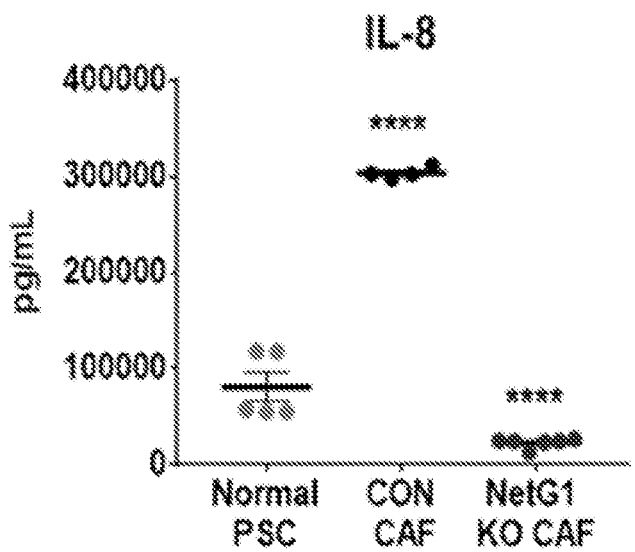
Figure 11:
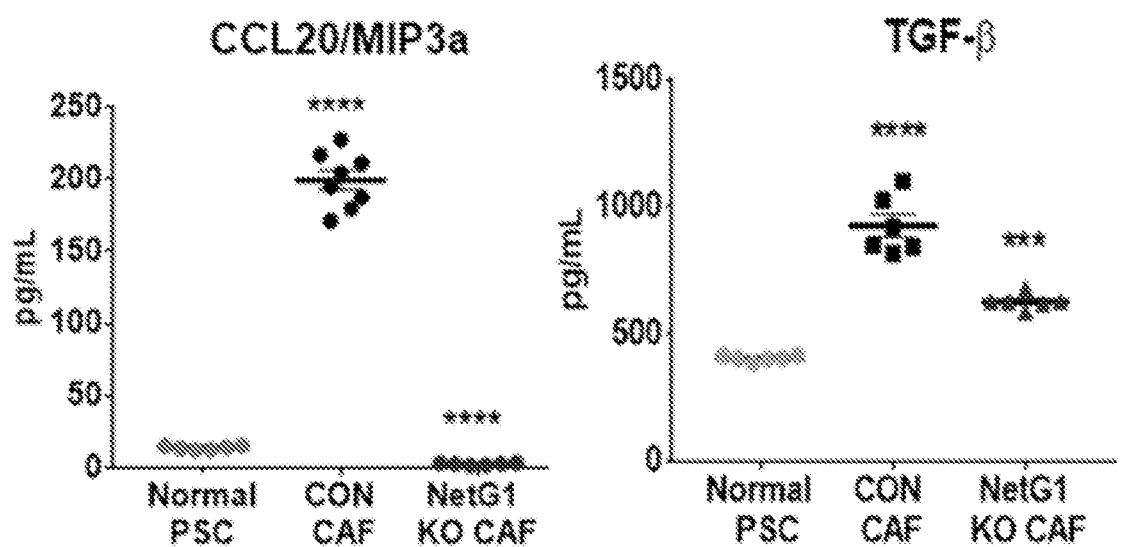
Figure 11:
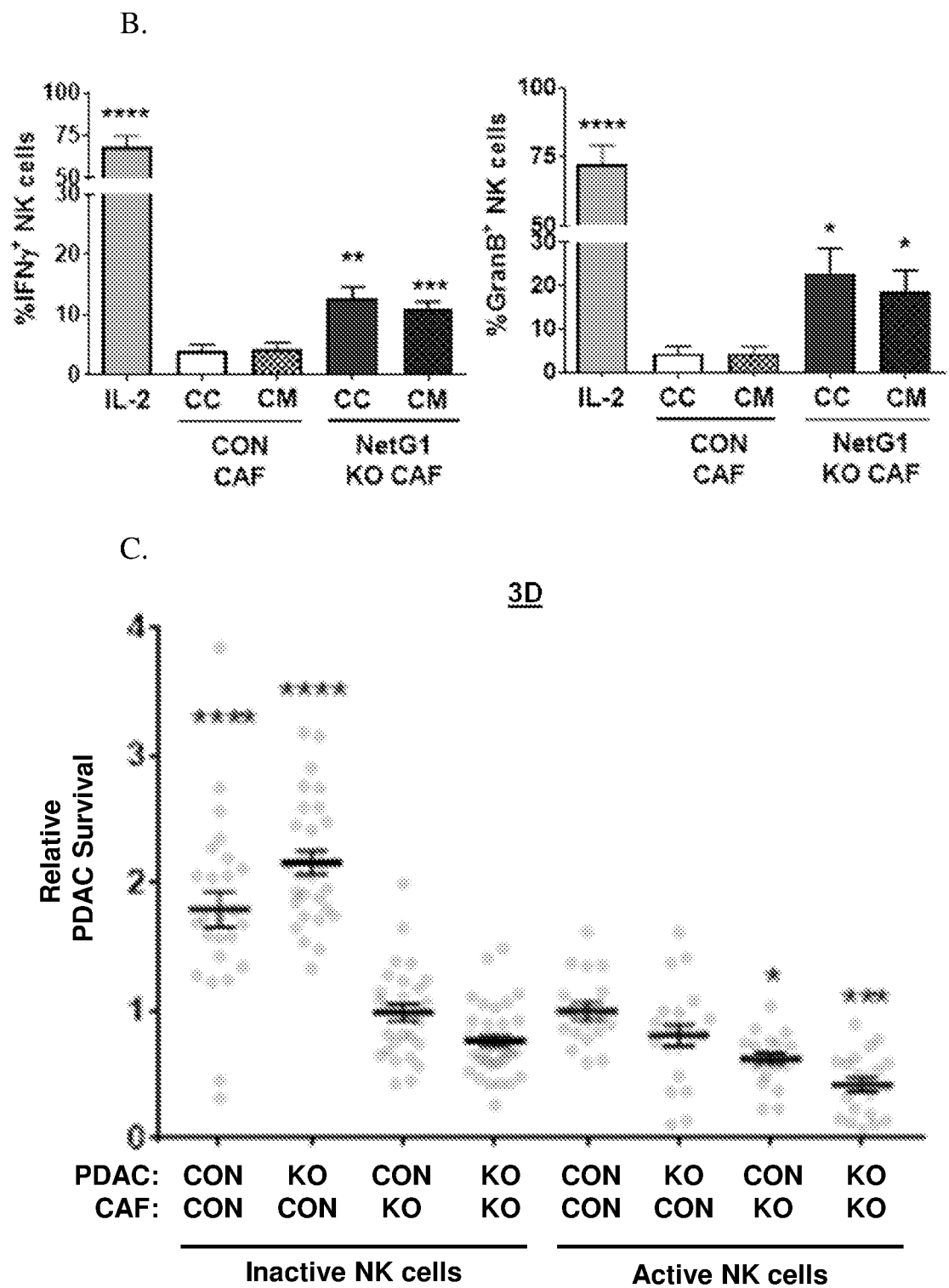
Figure 11:
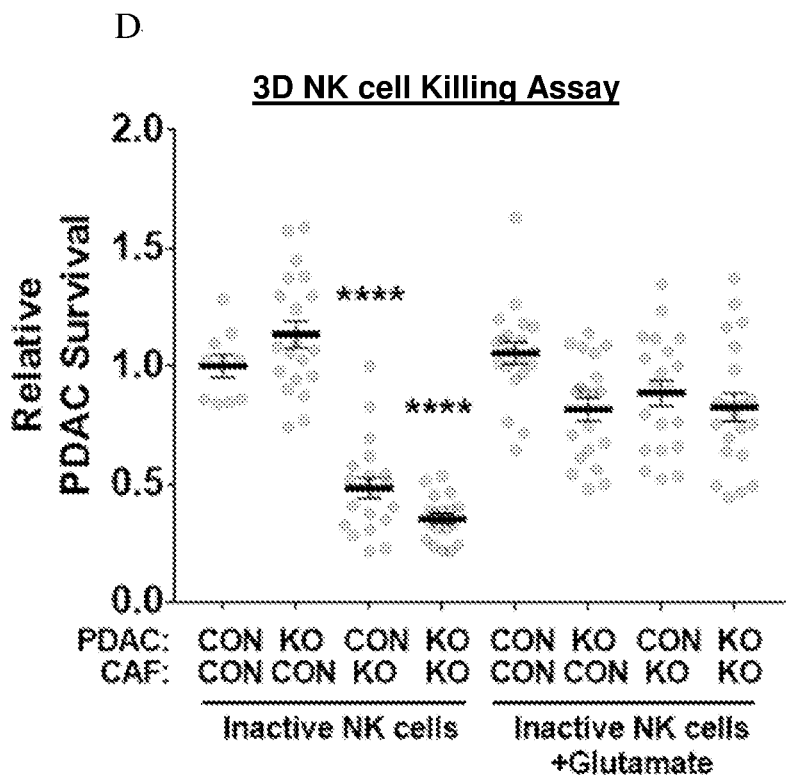
Figure 11:
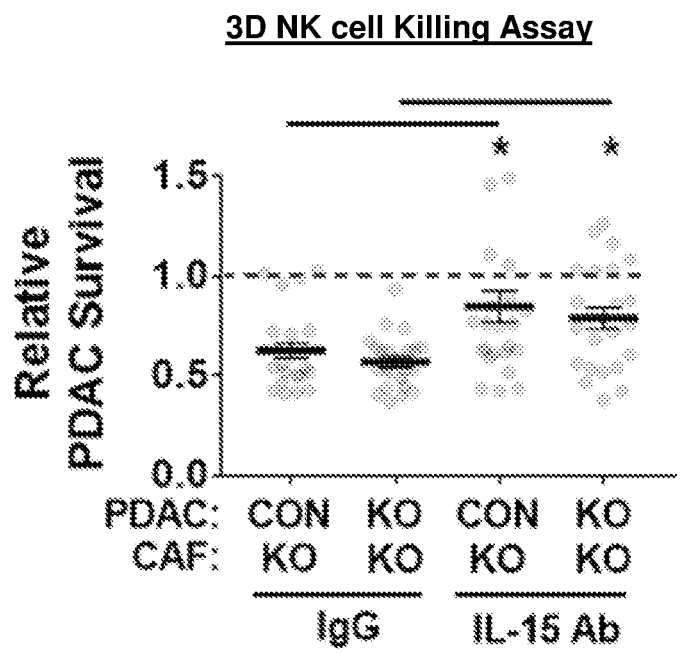

Example 7: Knockout of NetG1 in CAFs Reduces Immunosuppressive Cytokine Secretion Knockout of NetG1 in CAFs reduced immunosuppressive cytokine secretion, and CAFs protected PDAC from NK cell induced death in a NetG1/NGL1-dependent manner. Referring to FIG. 11 (panel A), a panel of immunosuppressive and pro-tumor cytokines (GM-CSF, IL-1Beta, CCL20, IL-6, IL-8, TGF-beta) and NK stimulating cytokine (IL-15) was performed. Knockout of NetG1 in CAFs produced less of all cytokines tested, but still produced significant levels of the anti-tumor NK cell cytokine IL-15. Referring to FIG. 11 (panel B), an assay was performed with Granzyme B and IFN-g production in NK cells stimulated with IL-2+IFN-γ (positive controls) or in co-culture conditions with conditioned media or direct contact with CAFs (CON vs knockout of NetG1). Knockout of NetG1 in CAF media or direct contact partially activated NK cells. Referring to FIG. 11 (panel C), an NK cell killing assay in 3D (CAF ECM) was carried out. Knockout of NetG1 in CAFs allowed NK cells to kill PDAC, while CON CAFs protected PDAC. Referring to FIG. 11 (panel D), glutamate addition to CAFs in which NetG1 was knocked out partially restored protection upon PDAC from NK cell-induced death, signifying a metabolic link between glutamate production from CAFs and anti-tumor NK cell immunity. Referring to FIG. 11 (panel E), the blockage of IL-15 rescues PDAC cells from NK cell induced death in the presence of NetG1 knockout CAFs, indicating that IL-15 is involved in the immunosuppressive activity of CAFs.

Figure 12:
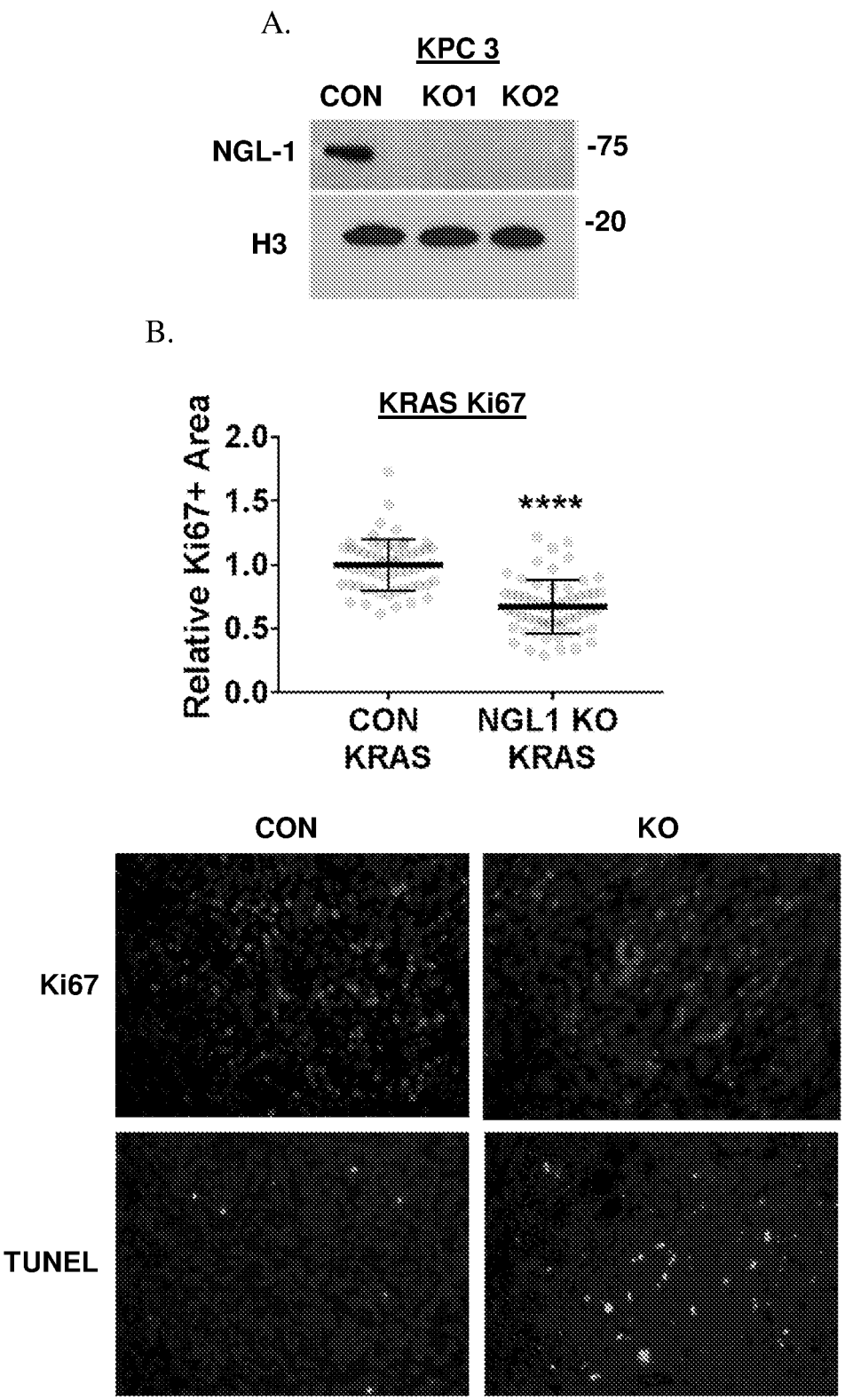
FIG. 12 (panels A and B) knockout of NGL1 in PDAC tumors are less aggressive, proliferate less and are more prone to death, due to increased cytotoxic immune cell infiltration.

Knockout of NGL1 in PDAC tumors were less aggressive and more prone to death, due to increased cytotoxic immune cell infiltration. Referring to FIG. 12 (panel A), a blot of NGL1 in aggressive murine PDAC cells was obtained, and indicated successful knockout of NGL1 by CRISPR/Cas9. Referring to FIG. 12 (panel B), NGL-1 knockout PDAC cells tend to proliferate less (lower proliferative index, Ki67 staining). FIG. 12 (panel C) representative images of Ki67 and TUNEL assays from CON and knockout tumor tissue were obtained.

Example 8: Murine Orthotopic Model of PDAC

Figure 13:
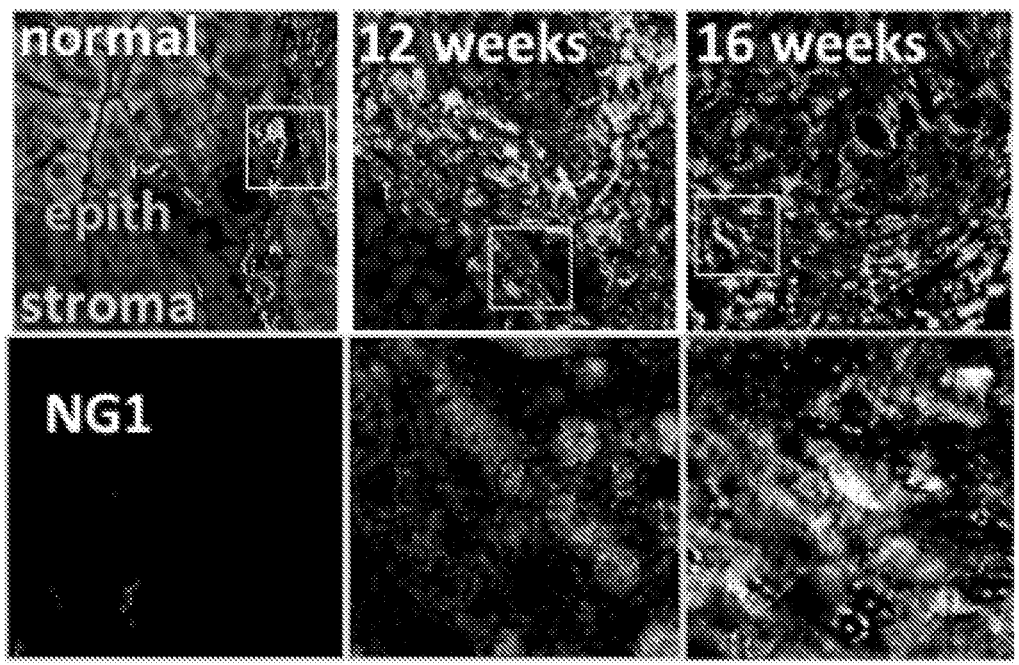
FIG. 13 (panels A, B, C, D and E) show that a murine orthotopic model of PDAC recapitulates in vitro results and demonstrates that NetG1/NGL1 axis is involved in PDAC progression and differentiation, with less proliferation and more death when NGL-1 is absent in the PDAC cells.
Figure 13:
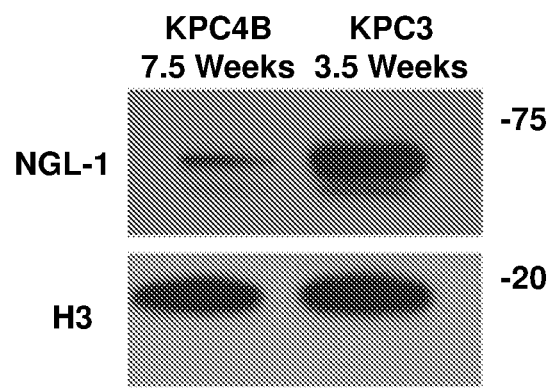
Figure 13:
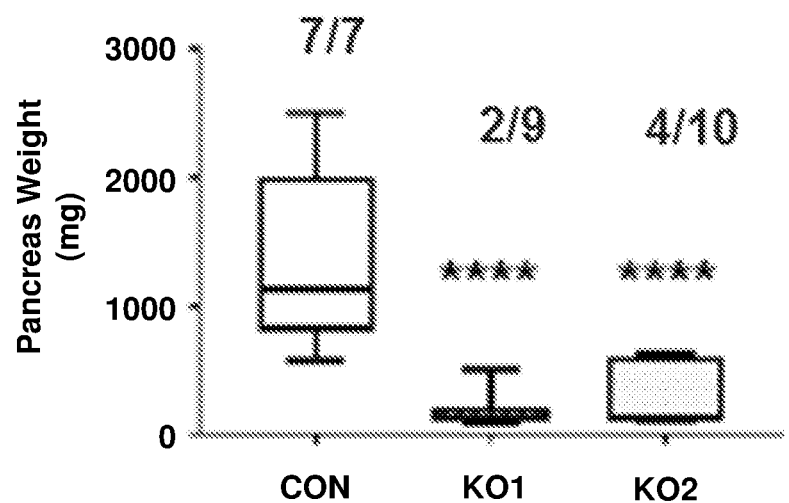
Figure 13:
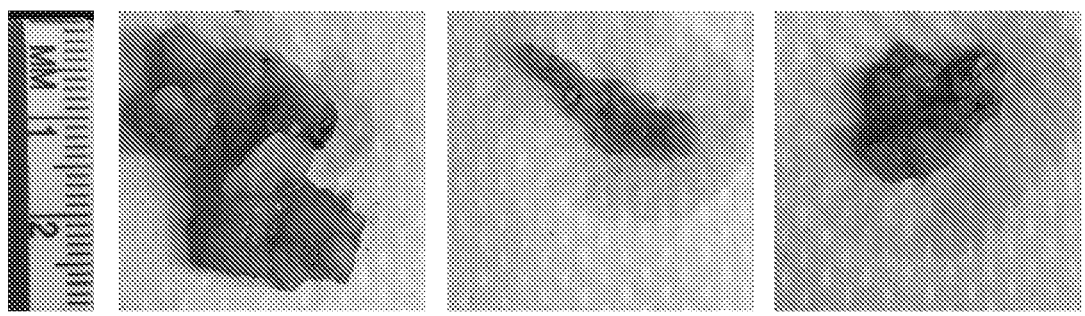
Figure 13:
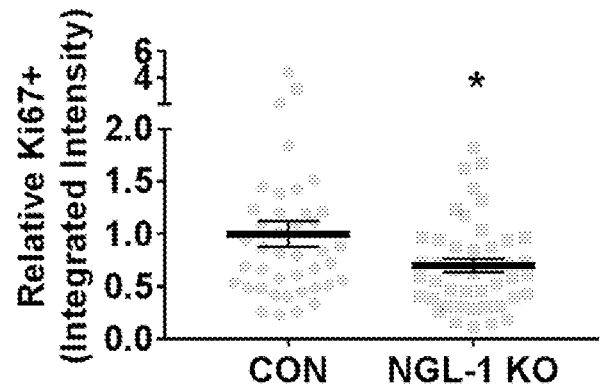
Figure 13:
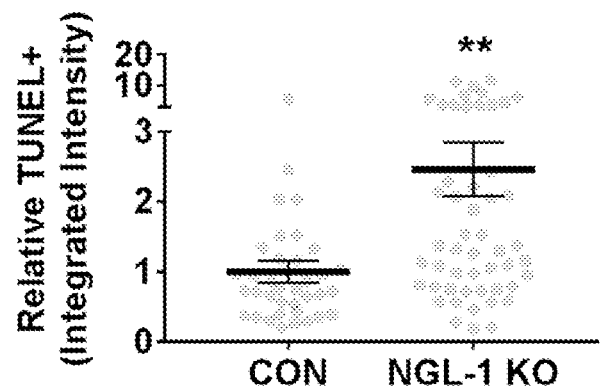
Figure 13:
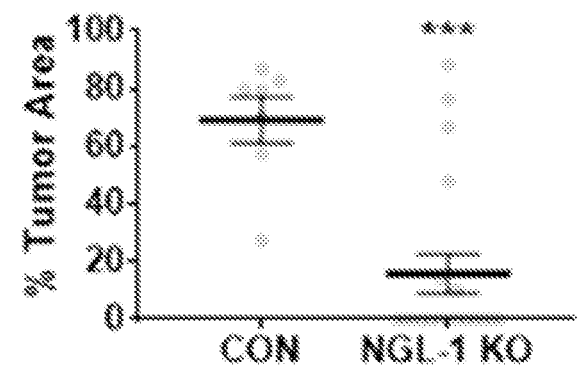
Figure 13:
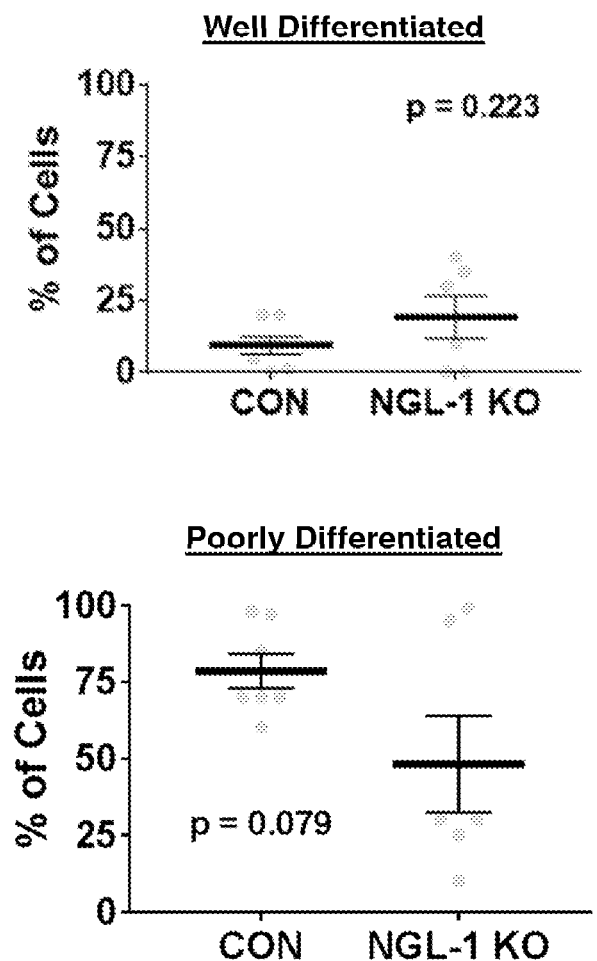
Figure 13:
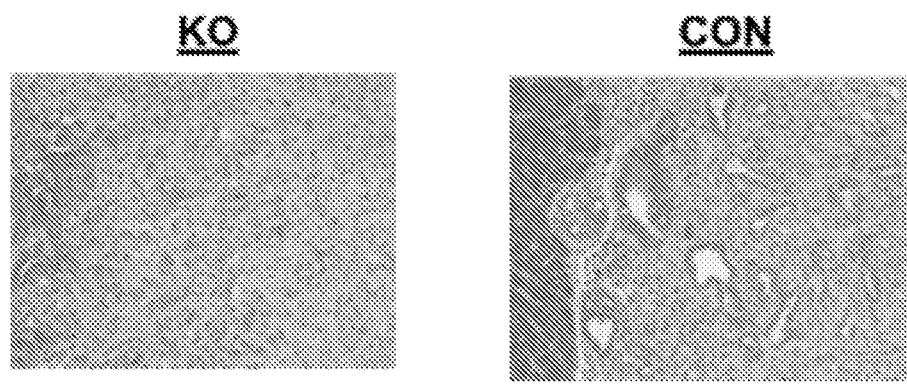
Figure 14:
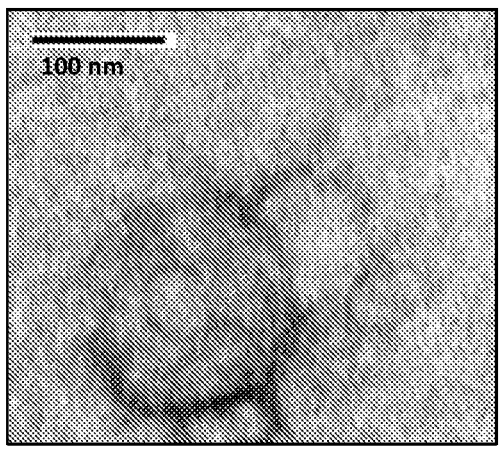
FIG. 14 (panels A-D) A; extracellular vesicles (EVs) collected from C1 vs C2 CAFs showing increased levels of NetG1 in small microvesicles that differ from activated α5β1-integrin positive exosomes (identify by expression of CD81, not shown). B; The figure also shows that extracellular vesicles collected from intact CAFs can rescue PDAC cells from starvation but not the ones isolated from NetG1-KO CAFs. C; Further the figure suggests that upon tumoral NGL1 loss, CAF generated EVs regardless of the type of CAF producing the EVs, can no longer rescue these cells from starvation. D; Finally, engaging tumoral NGL1 with soluble NetG1 partially rescues PDAC cell death induced by starvation in the presence of EVs generated by NetG1$^{KO}$-CAFs. This figure suggests not only that the assorted vesicles could serve as biomarkers to detect "bad" desmoplasia/fibrosis in circulation but also that NetG1 expressed on microvesicles are needed for PDAC rescue from starvation induced death.
Figure 14:
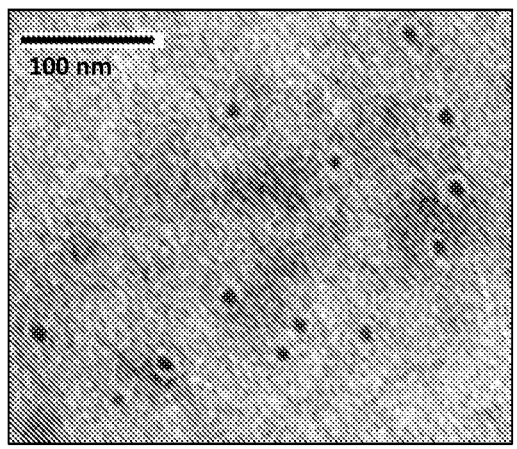
Figure 14:
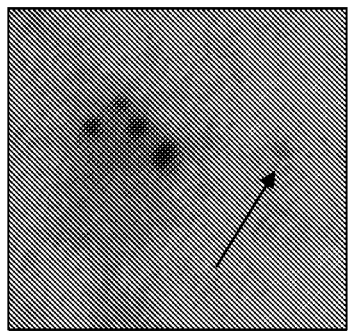
Figure 14:
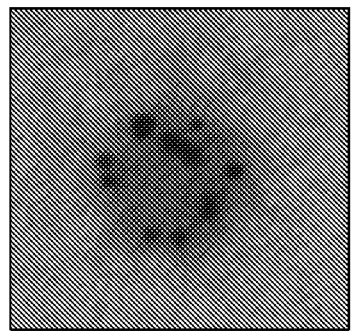
Figure 14:
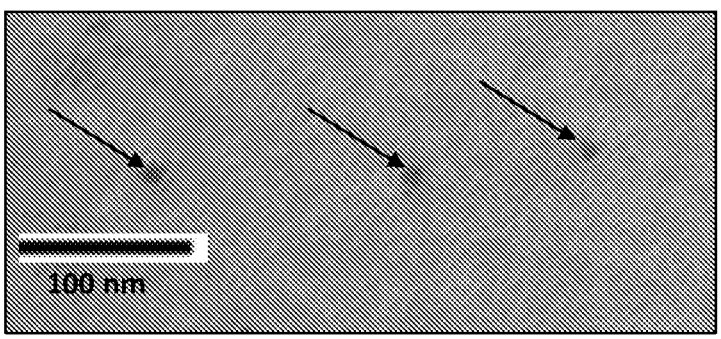
Figure 14:
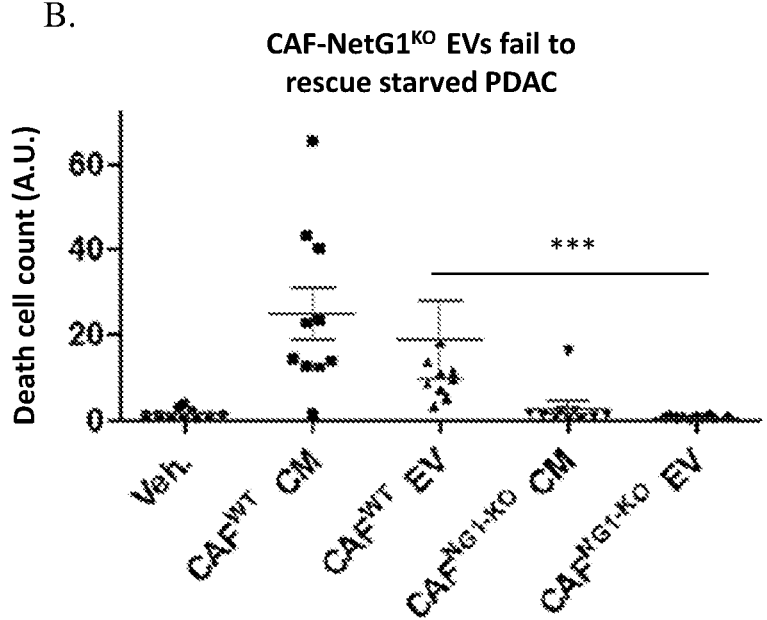
Figure 14:
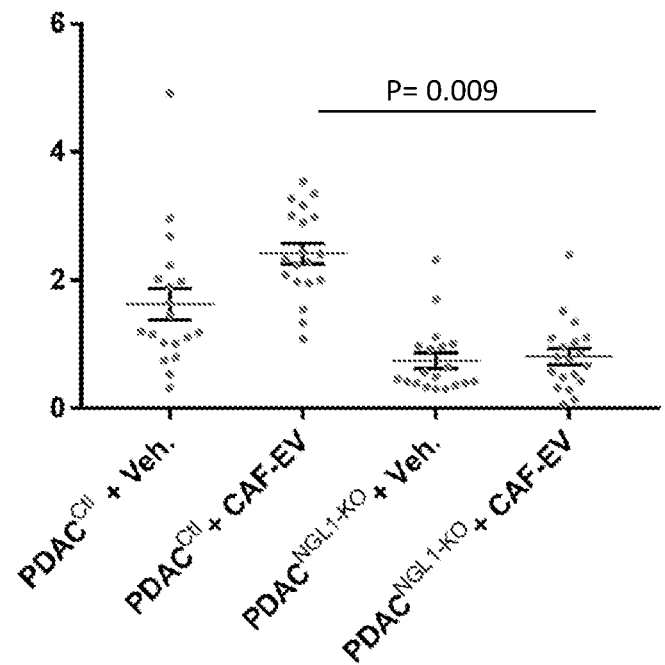
Figure 14:
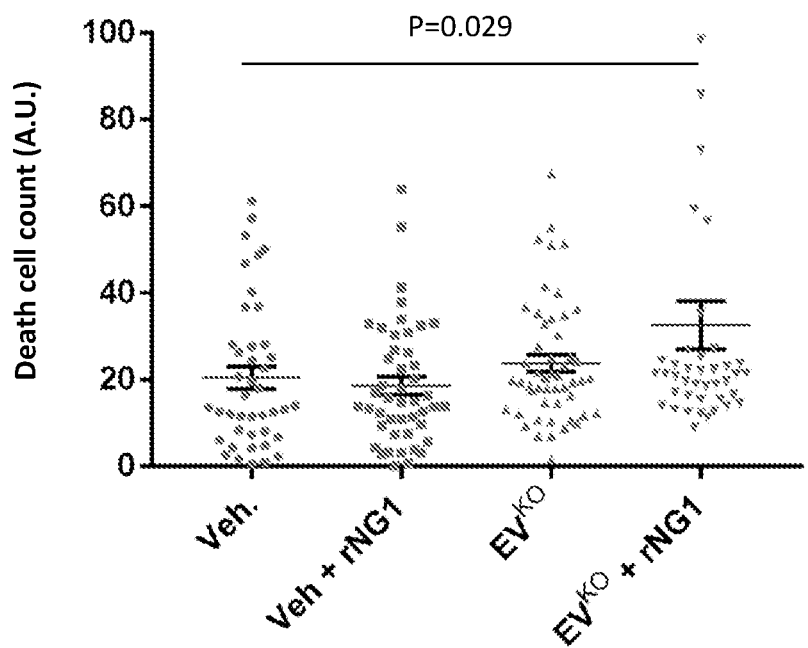

A murine orthotopic model of PDAC was produced, which recapitulated in vitro results, demonstrating that the NetG1/NGL1 axis is involved in PDAC progression (including immune responses). Referring to FIG. 13 (panel A), NetG1 was upregulated in the stroma of a spontaneous murine model of PDAC (KC model) and in aggressive murine PDAC cells derived from spontaneously arising PDAC tumors. Referring to FIG. 13 (panel B), from the orthotopic model of aggressive murine PDAC cells from panel A, knockout of NGL1 cells from aggressive cell lines have reduced incidence of tumor formation (red numbers) compared to control and have significantly less pancreas weight, indicative of decreased tumorigenic capacity. Referring to FIG. 13 (panel C), knockout of NGL1 in tumors have a lower proliferative index (Ki67 staining) and more death (TUNEL staining). Referring to FIG. 13 (panel D), pancreata from mice injected with NGL-1 knockout KPC3 tumors cells present less tumoral areas. Referring to FIG. 13 (panel E), NGL-1 knockout tumors are in greater percentage well differentiated and tumors expressing NGL-1 are poorly differentiated, which is detrimental for the patient.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating a human subject to induce desmoplastic stroma to express a normal phenotype comprising:
    detecting the level of NetG1 in desmoplastic stroma isolated from a human subject;
    detecting the level of NetG1 in circulating extracellular vesicles; or,
    detecting the level of pFAK in the desmoplastic stroma;
    wherein if the level of NetG1 in the desmoplastic stroma is increased relative to the level of NetG1 in normal stroma, or the level of NetG1 in the circulating extracellular vesicles is increased relative to the level in a normal individual, or the level of pFAk is increased relative to normal stroma, treating the human subject with a therapeutic regimen that inhibits fibroblast activation.

2. The method according to claim 1, wherein the NetG1 is NetG1m, NetG1a, NetG1c, NetG1n, NetG1o, NetG1b, NetG1 d, NetG1e, NetG1l or any other NetG1 isoform or splice variant.

3. The method according to claim 1, wherein the step of detecting the level of NetG1 comprises contacting the isolated desmoplastic stroma with an antibody that specifically binds to NetG1 or with soluble NGL1 that specifically binds to NetG1 or any other molecule with specific binding properties to NetG1.

4. The method according to claim 1, further comprising administering Vitamin D to the subject.

* * * * *